(12) United States Patent
Henao et al.

(10) Patent No.: US 9,353,023 B2
(45) Date of Patent: May 31, 2016

(54) CATALYTIC ALKANE CONVERSION AND OLEFIN SEPARATION

(71) Applicant: ExxonMobil Chemical Patents Inc., Baytown, TX (US)

(72) Inventors: Juan D. Henao, Houston, TX (US); Paul F. Keusenkothen, Houston, TX (US); Abhimanyu O. Patil, Westfield, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 154 days.

(21) Appl. No.: 14/469,227

(22) Filed: Aug. 26, 2014

(65) Prior Publication Data

US 2015/0065767 A1    Mar. 5, 2015

Related U.S. Application Data

(60) Provisional application No. 61/872,175, filed on Aug. 30, 2013.

(51) Int. Cl.
*C07C 5/327* (2006.01)
*C07C 5/333* (2006.01)
(Continued)

(52) U.S. Cl.
CPC .................. *C07C 2/84* (2013.01); *B01J 8/0207* (2013.01); *B01J 15/005* (2013.01); *B01J 19/24* (2013.01); *B01J 19/245* (2013.01); *C07C 2/08* (2013.01); *C07C 2/42* (2013.01); *C07C 2/78* (2013.01);
(Continued)

(58) Field of Classification Search
CPC ............ C07C 5/327; C07C 5/333; C07C 7/12
USPC .......................... 585/943, 654, 656, 658, 820
See application file for complete search history.

(56) References Cited

U.S. PATENT DOCUMENTS 3,435,089 A    3/1969    Walker et al.
4,144,277 A    3/1979    Walker et al.
(Continued)

FOREIGN PATENT DOCUMENTS

DE    275 452    1/1990
FR    1 588 738    4/1970
(Continued)

OTHER PUBLICATIONS

Aguado et al., "*Absolute Molecular Sieve Separation of Ethylene/Ethane Mixtures with Silver Zeolite A*," Journal of the American Chemical Society 2012, vol. 134, pp. 14635-14637.
(Continued)

*Primary Examiner* — Thuan D Dang

(57) ABSTRACT

Disclosed is a hydrocarbon conversion process that is less energy intensive than comparable processes. The hydrocarbon conversion process is particularly desirable for converting alkanes, such as methane into $C_{2+}$ olefins, such as ethylene and propylene, particularly with increasing selectivity to ethylene production. It is also desirable for effectively removing a $C_2$ composition (i.e., ethane, ethylene and/or acetylene) produced from the catalytic conversion of hydrocarbon comprised of $C_{2+}$ olefins. In addition, the hydrocarbon process is desirable for providing a substantially non-cryogenic separation of the desired $C_2$ compositions from the hydrocarbons (e.g., methane) present in the reaction mixture.

8 Claims, 3 Drawing Sheets

(51) Int. Cl.

| | |
|---|---|
| C07C 7/12 | (2006.01) |
| C07C 2/84 | (2006.01) |
| B01J 8/02 | (2006.01) |
| C07C 2/42 | (2006.01) |
| B01J 19/24 | (2006.01) |
| C07C 2/08 | (2006.01) |
| C07C 5/48 | (2006.01) |
| C07C 7/00 | (2006.01) |
| B01J 15/00 | (2006.01) |
| C07C 2/78 | (2006.01) |
| B01D 53/04 | (2006.01) |

(52) U.S. Cl.
CPC . *C07C 5/48* (2013.01); *C07C 7/005* (2013.01); *C07C 7/12* (2013.01); *B01D 53/04* (2013.01); *B01D 2256/24* (2013.01); *B01D 2257/7022* (2013.01); *B01D 2259/4009* (2013.01); *B01J 2208/0053* (2013.01); *B01J 2208/00309* (2013.01); *B01J 2208/00548* (2013.01); *B01J 2208/00557* (2013.01); *B01J 2208/00566* (2013.01); *B01J 2219/24* (2013.01); *B01J 2219/2402* (2013.01); *Y02P 20/51* (2015.11)

(56) References Cited

U.S. PATENT DOCUMENTS

| | | | |
|---|---|---|---|
| 4,751,336 | A | 6/1988 | Jezl et al. |
| 4,754,093 | A | 6/1988 | Jezl et al. |
| 4,754,095 | A | 6/1988 | Coughenour et al. |
| 4,988,660 | A | 1/1991 | Campbell |
| 5,095,161 | A | 3/1992 | Abrevaya et al. |
| 5,336,825 | A | 8/1994 | Choudhary et al. |
| 5,936,135 | A | 8/1999 | Choudhary et al. |
| 6,096,934 | A | 8/2000 | Rekoske |
| 6,258,993 | B1 | 7/2001 | Carr et al. |
| 7,022,888 | B2 | 4/2006 | Choudhary et al. |
| 2002/0020113 | A1 | 2/2002 | Kennedy et al. |
| 2010/0290978 | A1 | 11/2010 | Chun et al. |
| 2011/0315012 | A1 | 12/2011 | Kuznicki et al. |
| 2011/0320176 | A1 | 12/2011 | Haldoupis et al. |
| 2014/0018589 | A1 | 1/2014 | Iyer et al. |
| 2015/0065769 | A1 | 3/2015 | Henao et al. |
| 2015/0065771 | A1 | 3/2015 | Keusenkothen |
| 2015/0065773 | A1 | 3/2015 | Henao et al. |

FOREIGN PATENT DOCUMENTS

| | | |
|---|---|---|
| GB | 855 764 | 12/1960 |
| WO | WO 91/04240 | 4/1991 |
| WO | WO 95/20556 | 8/1995 |
| WO | WO 02/24614 | 3/2002 |
| WO | WO 2007/075945 | 7/2007 |
| WO | WO 2011/149996 | 12/2011 |

OTHER PUBLICATIONS

Ghose et al., "Solution Combustion Synthesized Catalytic Materials for Oxidative Coupling of Methane," 23$^{rd}$ North American Catalysis Society Meeting, Jun. 5, 2013. (Extended Abstract).
Jiang et al., "Methane to Ethylene with 85 Percent Yield in a Gas Recycle Electrocatalytic Reactor-Separator," Science, Jun. 10, 1994, vol. 264, pp. 1563-1566.
Keller et al., "Synthesis of Ethylene via Oxidative Coupling of Methane," Journal of Catalysis, vol. 73 (1982), pp. 9-19.
Korf et al., "The Development of Doped Li/MgO Catalyst Systems for the Low-Temperature Oxidative Coupling of Methane", Methane Conversion by Oxidative Processes—Fundamental and Engineering Aspects, Van Nostrand Reinhold / Springer, US, pp. 168-199, 1992.
Kruglov et al. "Optimization of the Simulated Countercurrent Moving-Bed Chromatographic Reactor for the Oxidative Coupling of Methane," Chemical Engineering Science, vol. 51, No. 11 (1996), pp. 2945-2950.
Liu et al., "Autothermal Reforming of Methane in a Reverse-Flow Reactor", Chemical Engineering & Technology, vol. 32, No. 9, Sep. 1, 2009, pp. 1358-1366.
Machocki et al., "Methane Oxidative Coupling in an Undiluted Reactor Mixture in a Reactor-Adsorber System With Gas Recirculation," Applied Catalysis A: General 146 (1996), pp. 391-400.
Mattisson, T., "Materials for Chemical-Looping with Oxygen Uncoupling," Hindawi Publishing Corporation, ISRN Chemical Engineering, vol. 2013, Article ID 526375, 19 pages, 2013.
Mehdipour et al., "Modeling of a PSA-TSA Process for Separation of $CH_4$ from $C_2$ Products of OcM Reaction," Separation Science and Technology, vol. 47, No. 8 (2012), pp. 1199-1212.
Mleczko et al., "Catalytic Oxidative Coupling of Methane—Reaction Engineering Aspects and Process Schemes," Fuel Processing Technology, vol. 42, No. 2-3 (1995), pp. 217-248.
Mortazavi et al., "Catalytic Methane Coupling Under Periodic Operation", The Canadian Journal of Chemical Engineering, vol. 74, No. 5, Oct. 1, 1996, pp. 683-694.
Olivier et al., "High-Temperature Parallel Screening of Catalysts for the Oxidative Coupling," Catalysis Today, vol. 137 (2008), pp. 80-89.
SRI, Ethylene from Methane, Process Economics Program Report No. 208 (Jan. 1994), 139 pages.
Tonkovich et al., "Enhanced $C_2$ Yields from Methane Oxidative Coupling by Means of a Separative Chemical Reactor," Science, vol. 262, No. 5131 (1993), pp. 221-223.
Veser et al., "Multiscale Process Intensification for Catalytic Partial Oxidation of Methane: From Nanostructured Catalysts to Integrated Reactor Concepts", Catalysis Today, Elsevier, NL, vol. 157, No. 1-4, Nov. 17, 2010, pp. 24-32.
Yentekakis et al., "Oxidative Coupling of Methane to Ethylene with 85% Yield in a Gas Recycle Electrocatalytic Reactor Separator," Studies in Surface Science and Catalysis, vol. 107 (1997), pp. 307-312.
Bloch et al., "Hydrocarbon Separations in a Metal Organic Framework with Open Iron(II) Coordination Sites," Science, vol. 335, pp. 1606-1610, 2012.
Centi et al., "Direct Conversion of Methane, Ethane and Carbon Dioxide to Fuels and Chemicals," The Catalyst Group Resources Inc., Spring House, 2008.
Choudhary et al., "Low-Temperature Nonoxidative Activation of Methane over H-Galloaluminosilicate (MFI) Zeolite," Science, vol. 275, pp. 1286-1288, 1997.
Choudhary et al., "Product Selectivity and Aromatics Distribution in Aromatization of Propane Over H—GaMFI Zeolite: Influence of Temperature," Microporous and Mesoporous Materials, vol. 23, Issues 3-4, pp. 231-238, 1998.
Das et al., "Interplay of Metalloligand and Organic Ligand to Tune Micropores within Isostructural Mixed-Metal Organic Frameworks (M'MOFs) for Their Highly Selective Separation of Chiral and Achiral Small Molecules," Journal of the American Chemical Society, vol. 134, Issue 20, pp. 8703-8710, 2012.
Gucuyener et al., "Ethane/Ethene Separation Turned on Its Head: Selective Ethane Adsorption on the Metal-Organic Framework ZIF-7 through a Gate-Opening Mechanism," Journal of the American Chemical Society, vol. 132, Issue 50, pp. 17704-17706, 2010.
Guo et al., "Dehydrogenation and Aromatization of Propane over Rhenium-Modified HZSM-5 Catalyst," Journal of Molecular Catalysis A: Chemical, vol. 239, Issue 1-2, pp. 222-227, 2005.
Guo et al., "Energy Efficient Coaromatization of Methane and Propane," Journal of Natural Gas Chemistry, vol. 18, Issue 3, pp. 260-272, 2009.
He et al., "High Separation Capacity and Selectivity of $C_2$ Hydrocarbons over Methane with a Microporous Metal-Organic Framework at Room Temperature," Chemistry—A European Journal, vol. 18, Issue 7, pp. 1901-1904, 2012.
Liu et al., "Scale Up and Stability Test for Oxidative Coupling of Methane Over $Na_2 WO_4$ -$Mn/SiO_2$ Catalyst in a 200 ml Fixed-Bed Reactor," Journal of Natural Gas Chemistry, vol. 17, No. 1, pp. 59-63, Mar. 2008.
Tonkovich et al., "A Simulated Countercurrent Moving-Bed Chromatographic Reactor for the Oxidative Coupling of Methane: Experimental Results," Chemical Engineering Science, vol. 49, No. 24, pp. 4647-4656, 1994.

CATALYTIC ALKANE CONVERSION AND OLEFIN SEPARATION

CROSS-REFERENCE TO RELATED APPLICATION

This application claims priority to and the benefit of (i) U.S. Provisional Patent Application No. 61/872,175, filed Aug. 30, 2013; (ii) E.P. Patent Application No. 13189746.4, filed Oct. 22, 2013; the contents of which are incorporated herein by reference in their entireties. The following related cases are also incorporated by reference in their entireties: (i) P.C.T. Patent Application No. PCT/US2014/052710, filed Aug. 26, 2014; (ii) U.S. patent application Ser. No. 14/469,141, filed Aug. 26, 2014, (iii) P.C.T. Patent Application No. WO2015/031366, filed Aug. 26, 2014; (iv) U.S. patent application Ser. No. 14/469,180, filed Aug. 26, 2014; (v) P.C.T. Patent Application No. PCT/US2014/052698, filed Aug. 26, 2014; (vi) U.S. patent application Ser. No. 14/469,109, filed Aug. 26, 2014; and (vii) U.S. patent application Ser. No. 14/469,227, filed Aug. 26, 2014.

FIELD OF THE INVENTION

The invention relates to catalytically converting alkane and oxidant to produce unsaturated hydrocarbon. The invention further relates to processes for catalytically converting alkane to produce $C_{2+}$ unsaturates, to equipment useful in such processes, and to processes for removing a $C_2$ composition produced from the catalytic conversion.

BACKGROUND OF THE INVENTION

Producing ethylene by methane dehydrogenation is an energy-intensive reaction. Since the reaction is endothermic and reaction temperatures greater than 800° C. are generally required to achieve practical methane conversion levels, a significant amount of heat is required to maintain the reaction. Generating this heat and transferring it to the methane is a significant cost and can introduce inefficiencies into the process. In order to overcome some of these difficulties, there has been considerable effort directed toward methane conversion via catalytic oxidative coupling reactions.

One process for producing ethylene from methane by catalytic oxidative coupling is disclosed in *Synthesis of Ethylene via Oxidative Coupling of Methane*, G. E. Keller and M. H. Bhasin, Journal of Catalysis 73, 9-19 (1982). Although an appreciable selectivity to ethylene was observed (to a maximum of about 50%), conversion was relatively low. In order to overcome the methane-ethylene separation difficulties resulting from the low methane conversion, technology has been developed for quenching the reaction product downstream of the oxidative coupling reactor, and then separating ethylene from the unreacted methane.

One process, disclosed in *Enhanced $C_2$ Yields from Methane Oxidative Coupling by Means of a Separative Chemical Reactor*, A. E. Tonkovich, R. W. Carr, R. Aris, Science 262, 221-223, 1993, includes a simulated countercurrent moving-bed chromatographic reactor, and achieves 65% methane conversion and 80% selectivity to $C_2$ hydrocarbons. The reactor is configured in four sections, with each section comprising (i) a catalytic reactor containing $Sm_2O_3$ catalyst and (ii) an adsorbent column located downstream of the catalytic reactor. Methane and oxygen react via catalytic oxidative coupling in the reactor at a temperature in the range of about 900° K to 1100° K, and then ethylene is separated from unreacted methane in the sorption column. In order to maintain sufficient selectivity for ethylene sorption, the reactor's product is quenched to a temperature of 373° K in the sorption column. In another process, disclosed in *Methane to Ethylene with 85 Percent Yield in a Gas Recycle Electrocatalytic Reactor-Separator*, Y. Jiang, I. V. Yentekakis, C. G. Vayenas, Science 264, 1563-1566, 1994, gas recycle is utilized to further increase methane conversion, but an even lower quench temperature (30° C.) is used during ethylene sorption.

Although the disclosed moving-bed and gas-recycle processes improve conversion, the quenching is energy intensive, and further improvements are desired. Further improvements are particularly desired in converting alkanes such as methane into $C_{2+}$ olefins such as ethylene and propylene, particularly with increasing selectivity to ethylene production.

Separation of the $C_2$ components from the reaction mixture produced by the methane dehydrogenation process is also energy intensive in that cryogenic separation techniques are generally employed. Cryogenic separation involves the fractional distillation of components in a component mixture, in which the component mixture has been cooled to very low temperatures in order to separate the various components. Since methane dehydrogenation processes typically produce reaction mixtures comprising of multiple components such as ethylene, ethane, acetylene, propylene and carbon dioxide, as well as unreacted methane, and these types of components have very low boiling points, cryogenic separation is typically used in order to separate the individual components. Cryogenic separation generally requires refrigeration on the order of −150° C. to −100° C. in order to liquefy certain components, which is necessary in order to separate the various components. Thus, a substantial amount of energy is needed to reach appropriate cryogenic separation conditions.

U.S. Patent Pub. No. 2014/0018589 to Iyer et al. discloses systems and methods for reacting methane in an oxidative coupling of methane ("OCM") process to yield products comprising hydrocarbon compounds with two or more carbon atoms (also "$C_{2+}$ compounds"), and separating the products into streams for use in various downstream processes. The product stream is sent to a dryer to remove water, then to a nitrogen removal unit (NRU) to selectively adsorb nitrogen from the hydrocarbons by pressure swing adsorption. The remaining hydrocarbon product is then compressed and sent to a refrigeration unit to separate the $C_{3+}$, ethane, ethylene and methane components. The hydrocarbon products can be separated with less use of refrigeration, e.g., by using relatively smaller refrigeration units, provided water, $CO_2$, and nitrogen are removed from the reaction products. But even with these improvements, cryogenic (i.e., very low temperature) separation is still required to separate the particularly desired $C_2$ components and produce a $C_2$ rich product. It is desired to lessen or substantially eliminate the need for cryogenic separation, to achieve a more energy-efficient separation of the reaction mixture's $C_2$ components. In particular, further improvements are desired to achieve a substantially non-cryogenic separation of the $C_2$ components from the reaction mixtures.

SUMMARY OF THE INVENTION

This invention provides a more energy-efficient hydrocarbon conversion process than comparable processes. The hydrocarbon conversion process is particularly desirable for converting alkanes such as methane into $C_{2+}$ olefins such as ethylene and propylene, particularly with increasing selectivity to ethylene production. In addition, the hydrocarbon process is desirable for providing a substantially non-cryogenic separation of the $C_2$ components from the hydrocarbons (e.g., methane) present in the reaction mixture.

More particularly, the invention relates to a process for producing and isolating a $C_2$ composition. The process includes a step of providing a hydrocarbon reactant and an oxidant, wherein the hydrocarbon reactant comprises ≥10% alkane, e.g., methane, (molar basis, per mole of hydrocarbon reactant). At least a portion of the hydrocarbon reactant's alkane (e.g., methane) is catalytically converted in the presence of the oxidant and a hydrocarbon conversion catalyst to produce a reaction mixture comprising (A) a $C_2$ composition produced by the catalytic conversion, (B) water and/or $CO_2$ produced during the catalytic conversion, and (C) unconverted alkane (e.g., methane). The reaction mixture is exposed, under kinetic sorption conditions, to at least one sorbent to selectively remove from the reaction mixture at least a portion of the reaction mixture's $C_2$ composition to produce a $C_2$ lean mixture. The $C_2$ lean mixture comprises at least a portion of the unconverted alkane (methane) and has a $C_2$ content that is less than that of the reaction mixture. The sorbent comprises at least one $C_2$ selective sorbent. The reaction mixture is exposed to the $C_2$ selective sorbent a temperature of ≥50° C.

In certain aspects, the process further comprises selectively removing at least a portion of the reaction mixture's $CO_2$, the $CO_2$ removal being carried out before exposing the reaction mixture to the $C_2$ selective sorbent. Alternatively or in addition, the process can include a step of selectively removing from the reaction mixture at least a portion of any water, the water removal being carried out before exposing the reaction mixture to the $C_2$ selective sorbent. The process can further include a step of desorbing a desorb composition from the $C_2$ selective sorbent after step (c), wherein the desorb composition comprises methane, ethane, and ethylene, and exposing the desorb composition to at least one olefin-selective sorbent under kinetic sorption conditions to selectively remove from the desorb composition at least a portion of the desorb composition's ethylene.

In certain aspects, the hydrocarbon reactant comprises ≥90% methane and the conversion catalyst comprises at least one oxidative coupling catalyst. The hydrocarbon reactant can further comprise ≥1% $C_{2+}$ alkane (molar basis, per mole of hydrocarbon reactant) and the conversion catalyst comprises at least one oxidative coupling catalyst and at least one oxydehydrogenation catalyst.

In certain aspects, the oxidant comprises $O_2$ and the catalytic conversion is carried out at a methane:$O_2$ molar ratio of >2:1. Alternatively, the oxidant can comprise ≥20% $O_2$ (molar basis, per mole of oxidant) and the catalytic conversion can be carried out at a methane:$O_2$ molar ratio of ≥4:1.

In certain aspects, (i) the oxidant can comprise ≥90% $O_2$ (molar basis, per mole of oxidant), (ii) the hydrocarbon reactant can comprise ≥90% methane (molar basis, per mole of hydrocarbon reactant), and (iii) the hydrocarbon can further comprise ≥1% of one or more $C_2$ to $C_5$ linear, iso, and cyclo alkane (molar basis, per mole of hydrocarbon reactant).

In certain aspects, the $C_2$ selective sorbent comprises at least one transition metal that exhibits π-complexation with olefins and has an electron affinity ≥1.0 ev. The $C_2$ selective sorbent can include at least one shape-selective material. For example, the $C_2$ selective sorbent can include at least one molecular sieve. The $C_2$ selective sorbent can be an olefin-selective sorbent having chemoselectivity and shape selectivity.

In other aspects, the process for producing and isolating a $C_2$ composition comprises (a) providing first and second hydrocarbon reactants and first and second oxidants, wherein the first and second hydrocarbon reactants each comprise ≥10% methane (molar basis, per mole of hydrocarbon reactant) and the first and second oxidants each comprise $O_2$; and (b) catalytically converting at least a portion of the first hydrocarbon reactant in the presence of the first oxidant and a hydrocarbon conversion catalyst to produce a first reaction mixture comprised of (A) a $C_2$ composition produced by the catalytic conversion, (B) water and/or $CO_2$ produced during the catalytic conversion, and (C) unconverted methane. The reaction mixture is exposed to at least one sorbent under kinetic sorption conditions to selectively remove from the first reaction mixture at least a portion of the first reaction mixture's $C_2$ composition to produce a first $C_2$ lean mixture comprised of at least a portion of the unconverted methane. The catalytic conversion can be carried out in a first time interval, with further catalytic conversion being carried out in a second time interval following the first time interval. In the second time interval, a second reaction mixture is produced by catalytically converting at least a portion of the second hydrocarbon reactant in the presence of the second oxidant and the hydrocarbon conversion catalyst, with the second reaction mixture comprising (A) a $C_2$ composition produced by the catalytic conversion, (B) water and/or $CO_2$ produced during the catalytic conversion, and (C) unconverted methane. The second reaction mixture is exposed to at least one sorbent under kinetic sorption conditions to selectively remove from the second reaction mixture at least a portion of the second reaction mixture's $C_2$ composition to produce a second $C_2$ lean mixture.

Catalytic conversion can be carried out in a reverse-flow reactor. The reverse flow reactor can include first and second regions, the first region contains at least a portion of the hydrocarbon conversion catalyst, and the second region contains at least a portion of the $C_2$ selective sorbent.

Other aspects of the invention further relate to a hydrocarbon conversion system for producing a $C_2$ composition, which includes a reactor in fluid communication with a sorption system. The reactor comprises: (i) a first region having a first thermal mass and a first aperture, (ii) a second region having a second thermal mass and a second aperture, and (iii) a catalytic conversion zone containing catalyst having an oxidative coupling functionality, oxydehydrogenation functionality or both, with at least a portion of the catalyst being deposited on or in at least one of the first thermal mass and second thermal mass. The first and second regions are configured for flowing a feed mixture to enter the reactor proximate to the first aperture, with one or more components of a reaction mixture exiting the reactor proximate to the second aperture. A sorption system, which operates under kinetic sorption conditions, is configured to be in fluid communication with the second aperture for receiving at least a portion of the catalytically converted reaction mixture, The sorption system includes at least one $C_2$ selective sorbent.

In certain aspects of the hydrocarbon conversion system, the reactor is a reverse-flow reactor in which the first and second regions of the reverse-flow reactor are configured for flowing a first flow of a first feed mixture to enter the reactor proximate to the first aperture of the first thermal mass, with one or more components of a first reaction mixture exiting the reactor proximate to the second aperture of the second thermal mass. The reverse-flow reactor is further configured for flowing a second flow of a second feed mixture to enter the reactor proximate to the second aperture of the second thermal mass, with one or more components of the second reaction mixture exiting the reactor proximate to the first aperture.

Figure 1:
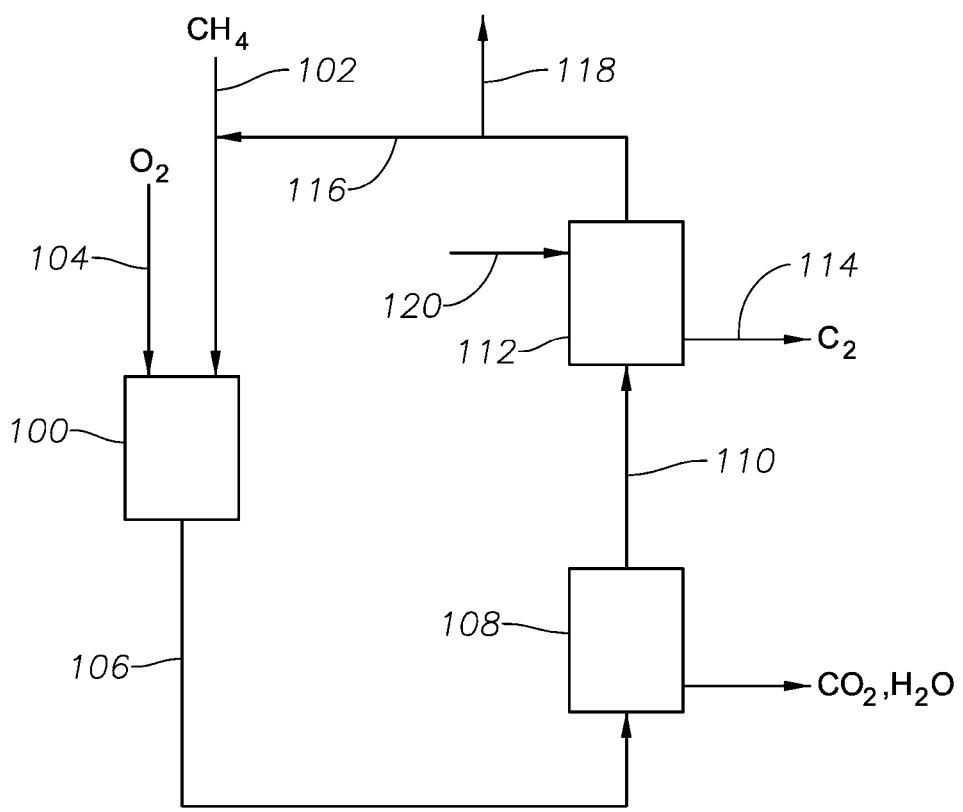
FIG. 1 is a simplified diagrammatic illustration of a generalized system for selectively removing a $C_2$ composition according to certain aspects of the invention.

Although the invention can be described in terms of a hydrocarbon conversion process, particularly an oxidative coupling reaction process, for producing olefins such as ethylene and propylene, the invention is not limited thereto. In other words, to the extent that the following detailed description is specific to a particular aspect or a particular use, this is intended to be illustrative only, and is not to be construed as limiting the scope of the invention. On the contrary, it is intended to cover all alternatives, modifications and equivalents that may be included within the spirit and scope of the invention.

DETAILED DESCRIPTION OF THE INVENTION

I. Introduction and Definitions

This invention is directed to a relatively low-energy process for removing, i.e., separating and recovering, a $C_2$ composition produced from the catalytic conversion of hydrocarbon. The catalytic conversion reaction involves catalytically converting alkane to produce $C_{2+}$ hydrocarbon, particularly $C_{2+}$ unsaturated hydrocarbon, and more particularly ethylene. The $C_2$ composition that is separated from the $C_{2+}$ hydrocarbon is predominantly $C_2$ unsaturated hydrocarbon, i.e., ethylene and optionally ethylene and/or acetylene. The process is highly efficient for converting alkane, such as methane, to produce the specified $C_2$ composition. The process is also highly energy efficient in that a substantial portion of the specified $C_2$ composition can be recovered without having to rely on energy-intensive cryogenic separation.

The hydrocarbon reactant and an oxidant are supplied to a reactor for carrying out the process. The hydrocarbon reactant comprises alkane, e.g., $C_{5-}$ alkane, such as methane. The hydrocarbon reactant can comprise a single component, e.g., methane. In aspects where the hydrocarbon reactant comprises a plurality of components, each component (e.g., methane and ethane) can be supplied to the reactor as a separate stream. In other aspects, the hydrocarbon reactant is provided to the reactor as a mixed stream.

At least a portion of the hydrocarbon reactant's alkane is catalytically converted in the presence of oxidant and a hydrocarbon conversion catalyst to produce a reaction mixture comprised of the specified $C_2$ composition, which is produced by the alkane conversion. While not wishing to be bound by any theory or model, it is believed that the conversion is primarily the result of (i) one or more oxidative coupling reactions when the hydrocarbon reactant comprises methane and/or (ii) one or more oxydehydrogenation reactions when the hydrocarbon reactant comprises $C_{2+}$ alkane.

Besides the $C_2$ composition, the reaction mixture typically further comprises unconverted alkane and/or $CO_2$ produced during the alkane conversion. At least a portion of the reaction mixture's $C_2$ composition is removed by exposing the reaction mixture to at least one $C_2$ selective sorbent. Using a $C_2$ selective sorbent allows the removal and recovery of $C_2$ components from the reaction mixture, especially ethylene, at temperatures $\geq 0°$ C., such as $\geq 50°$ C. In other words, using a $C_2$ selective sorbent substantially obviates the need for cryogenic separation of $C_2$ compounds from the reaction mixture.

Exposing the reaction mixture to at least one $C_2$ selective sorbent results in the selective sorption of at least a portion of the reaction mixture's $C_2$ composition. This produces a $C_2$ lean mixture, which comprises at least a portion of the unconverted alkane. The $C_2$ lean mixture is "lean" in the sense that it has a $C_2$ content that is less than that of the reaction mixture. Although optional, it is efficient to remove at least a portion of the reaction mixture's $CO_2$ upstream of the separating at least a portion of the reaction mixture's $C_2$ composition upstream of the $C_2$ selective sorbent. Doing so beneficially lessens the vapor loading on the $C_2$ selective sorbent, and also allows for the use of process equipment (e.g., conduits, sorbent containment vessels, compressors, etc.) of significantly smaller hydraulic capacity. For generally the same reasons, it is beneficial to remove any water present in the reaction mixture before the reaction mixture is exposed to the $C_2$ selective sorbent.

The specified hydrocarbon reactant is converted in at least one catalytic reactor. In certain aspects, the catalytic reactor comprises at least one reverse-flow catalytic reactor such as a tubular reverse-flow catalytic reactor. It is observed that selectivity to $C_2$ compositions and $C_{2+}$ olefins (particularly ethylene) can be increased when the hydrocarbon reactant's alkane comprises methane, e.g., when the hydrocarbon reactant comprises $\geq 10\%$ methane (molar basis, per mole of hydrocarbon reactant). Aspects of the invention relating to the catalytic conversion of a hydrocarbon reactant comprising $\geq 10\%$ methane (molar basis) in a tubular reverse flow catalytic reactor will now be described in more detail.

The invention additionally relates to a hydrocarbon conversion system and/or apparatus for producing a $C_2$ composition. The apparatus includes a reactor, such as a reverse-flow reactor and a $C_2$ selective sorption system. The reactor can comprise (i) a first region having a first thermal mass and a first aperture; (ii) a second region having a second thermal mass and a second aperture, and (iii) a catalytic conversion zone containing catalyst having an oxidative coupling functionality, oxydehydrogenation functionality or both, with at least a portion of the catalyst being deposited on or in at least one of the first thermal mass and second thermal mass. The first and second regions can be configured for flowing a first flow of a first feed mixture which enters the reactor proximate to the first aperture. One or more components of a first reaction mixture exit the reactor proximate to the second aperture. Optionally, the reactor can be further configured for flowing a second flow of a second feed mixture to enter the reactor proximate to the second aperture, with one or more components of the second reaction mixture exiting the reactor proximate to the first aperture. The $C_2$ selective sorption system is in fluid communication the first aperture, and optionally the second aperture, for receiving at least a portion of the catalytically converted reaction mixture, and optionally the second reaction mixture, with the $C_2$ selective sorption system including at least one $C_2$ selective sorbent.

The invention is not limited to these aspects, and this description is not meant to foreclose the use of other reactors and/or other hydrocarbon reactants within the broader scope of the invention. For the purpose of this description and appended claims, the following terms are defined:

A "$C_2$ selective sorbent" is a sorbent having a selectivity for [ethane+ethylene] sorption over that of methane that is greater than 1.0. When exposed under sorption conditions to a mixture comprising methane, ethane, and ethylene, $C_2$ selective sorbent having a selectivity for [ethane+ethylene] over methane of greater than 1.0 will retain >50% of the mixture's [ethane+ethylene] and ≤50% of the mixture's methane. When a $C_2$ selective sorbent has a selectivity for [ethane+ethylene] over that of methane of greater than 5.0, the sorbent will retain >83% of the mixture's [ethane+ethylene]. The $C_2$ selective sorbent can have, e.g., a selectivity for [ethane+ethylene] over methane ≥9, such as ≥99, or ≥999, or ≥9999.

An "olefin-selective sorbent" is a sorbent having a selectivity for ethylene sorption over that of ethane that is greater than 1.0. When exposed under sorption conditions to a mixture comprising ethane and ethylene, an olefin-selective sorbent having a selectivity for ethylene over ethane of greater than 1.0 will retain >50% of the mixture's ethylene and ≤50% of the mixture's ethane. When an olefin-selective sorbent has a selectivity for ethylene over ethane of greater than 5.0, the sorbent will retain >83% of the mixture's ethylene. The olefin-selective sorbent can have, e.g., a selectivity for ethylene over ethane ≥9, such as ≥99, or ≥999, or ≥9999.

A sorption carried out under "kinetic sorption conditions" is one where sorption is halted before equilibrium sorption conditions are achieved. Kinetic sorption conditions can be obtained, e.g., by operating the sorption at a higher rate per volume of sorbent, by shortening the length of the sorbent bed, etc.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "alkane" means substantially saturated compounds containing hydrogen and carbon only, e.g., those containing ≤1% (molar basis) of unsaturated carbon atoms. The term alkane encompasses $C_1$ to $C_5$ linear, iso, and cyclo alkanes.

The term "unsaturate" means a $C_n$ hydrocarbon containing at least one carbon atom directly bound to another carbon atom by a double or triple bond.

A $C_2$ composition can be considered a composition comprised of at least one compound containing two carbon atoms. For example, a $C_2$ composition can be a composition comprised of at least one compound selected from the group of ethane, ethylene and acetylene. Typically, the $C_2$ composition comprises ≥90% (molar basis, per mole of $C_2$ composition) of one or more of (i) ethane, (ii) ethylene, and (iii) acetylene, e.g., ≥95%, such as ≥99%. For example, the $C_2$ composition can comprise ≥90% of (i) ethane and (ii) ethylene, such as ≥95%, or ≥99%. The $C_2$ composition can be one that predominantly comprises $C_2$ unsaturates, e.g., ≥50% of (i) ethylene and/or (ii) acetylene, such as ≥75%, or ≥90%, or ≥99%, with the balance comprising ethane, e.g., <50% ethane, such as <25%, or ≤10%, or <1% ethane. One suitable $C_2$ composition comprises 50% to 99% ethylene, with the balance comprising ethane, e.g., 75% to 99% ethylene, or 90% to 99% ethylene.

The term "Periodic Table" means the Periodic Chart of the Elements, as it appears on the inside cover of The Merck Index, Twelfth Edition, Merck & Co., Inc., 1996.

The term "oxidant" means any oxygen-bearing material which, under the conditions in the reaction zone, yields an oxygen atom for oxidative coupling and/or oxydehydrogenation. While not wishing to be limited to theory, molecular oxygen atom may be provided as a reactive gas in a gaseous zone and/or atomic oxygen may be provided from a catalyst surface as, for instance, reacted, sorbed forms.

The term "oxidative coupling" refers to the oxygen-assisted dehydrogenation and coupling (formation of C—C bonds) of alkane (particularly methane) to produce water and hydrocarbon of higher order, such as producing $C_2$ hydrocarbon from methane.

The term "oxydehydrogenation" means oxygen-assisted dehydrogenation of an alkane, particularly a $C_{2+}$ alkane, to produce an equivalent alkene and water without coupling.

The term "hydrocarbon conversion catalyst" means any catalyst having at least one of oxidative coupling functionality and oxydehydrogenation functionality.

The term "residence time" means the average time duration for non-reacting (non-converting by oxidative coupling) molecules (such as He, $N_2$, Ar) having a molecular weight in the range of 4 to 40 to traverse the reactor or a defined zone within the reactor, such as a reaction zone of a oxidative coupling reactor.

The term "catalytic oxidative coupling reactor" means a reactor in which oxidative coupling and/or oxydehydrogenation reactions are carried out. Optionally, ≥30.0% of the heat utilized by the reactions are provided by heat transfer from reactor components, e.g., solid surfaces associated with the reactor, such as tubulars or bed materials; optionally ≥80.0% or ≥90.0% of the heat utilized by the reactions are provided by such heat transfer. Optionally, an exothermic reaction (e.g., combustion) occurs within the catalytic oxidative coupling reactor, e.g., for preheating and/or reheating the first and/or second thermal mass segments.

The term "reaction stage" or "reactor stage" means at least one catalytic oxidative coupling reactor, and optionally including means for conducting one or more feeds thereto and/or one or more products away therefrom.

With respect to reactors, the term "zone" or "region" means a location within a reactor, e.g., a specific volume within a reactor and/or a specific volume between two reactors.

A "reaction zone" or "reactor zone" is a volume within the reactor for conducting at least one of oxidative coupling and oxydehydrogenation.

A "sorption zone" or "sorbent zone" is a volume within the reactor for sorbing and/or desorbing desired products of the oxidative coupling reaction, such as the desired $C_2$ composition.

The term "flow-through reactor" refers to a reactor in which feed can flow through the reactor, with the oxidant and hydrocarbon reactant feeds coming into contact with the conversion catalyst and oxygen storage material as the feed flows through the reactor.

The term "tubular reactor" means an elongated, reactor vessel of substantially any cross-section, the vessel being configured to allow fluid flow into, though, and out of the vessel at via least first and second apertures, the first and second apertures being located proximate to opposed ends of the elongated reactor vessel.

The term "fixed-bed catalytic reactor" means a catalytic reactor having at least one bed of catalyst, wherein the catalyst is substantially retained within the bed.

II. Feed Compositions for Conversion

The hydrocarbon conversion process can be carried out by catalytically converting a hydrocarbon reactant in the presence of oxidant. The hydrocarbon reactant and oxidant can be components of a total feed provided to the reactor, which can further include diluent. Alkane, oxidant, and diluent can each be introduced into a reactor as one or more separate streams or as a premixed feed.

The feed mixture (e.g., first feed mixture in forward flow and/or second feed mixture in reverse flow) can comprise e.g., at least 10% (weight basis) of the total feed provided to the reactor. For example, the feed mixture can comprise at least 20%, or at least 30%, or at least 40%, of the total feed provided to the reactor. In certain aspects, the feed mixture comprises up to 98% of the total feed provided to the reactor. For example, the feed mixture can comprise up to 90%, or up to 80%, or up to 70% of the total feed provided to the reactor. The balance of the total feed can be diluent, for example.

Diluent typically comprises one or more inert materials. For example, the total feed to the reactor can be diluted with essentially inert fluid. Examples of inert fluid include, but are not limited to, steam, nitrogen, carbon dioxide or other fluids that are substantially unreactive with the hydrocarbon in the feed mixture. When diluted, the diluent can provide from 5% (weight basis) wt. % to 90% of the total feed to the reactor, or from 10% to 50%. Dilution can be carried out by adding diluent to one or more of the hydrocarbon reactant (e.g., to the alkane component), the oxidant, or the feed mixture. Examples of the alkane component of the first and/or second hydrocarbon reactant include $C_1$ to $C_5$ linear, iso, and cyclo alkanes. Specific examples include methane, ethane, propane, butane and pentane. Particular examples include methane, ethane and propane, with methane being a preferred component.

The oxidant typically comprises one or more fluids which yield oxygen under the specified hydrocarbon conversion conditions. Typically, the oxidant includes one or more of molecular oxygen ($O_2$), $O_2^-$, $O_2^=$, ionized oxygen atoms, nitrogen oxides such as $N_2O$, etc. Oxidant is typically in the vapor phase at the specified hydrocarbon conversion conditions, but this is not required, and in certain aspects liquid and/or solid oxidant can be used. The oxidant can comprise $O_2$, e.g., ≥90% $O_2$ (molar basis, per mole of oxidant), such as, ≥99%. For example, the oxidant can comprise $O_2$ in air, or $O_2$ obtained or derived from air, e.g., by separation. The oxidant can comprise (or consist essentially of, or consist of) air. When the oxidant comprises $O_2$ in air, the total feed generally comprises at least a portion of the air's molecular nitrogen as diluent. In other words, when the oxidant comprises molecular oxygen in air, other gasses in the air, such as molecular nitrogen, are considered to be diluent, and are not considered to be part of the oxidant.

Alkane and oxidant are typically provided to the reactor at a mole ratio of alkane to oxidant of ≥2:1 (e.g., total molar alkane content of feed to reactor:total molar oxygen content of feed to reactor of ≥2:1), e.g., ≥4:1. For example, the alkane and oxidant are provided to the reactor at a mole ratio of alkane to oxidant of about 2:1 to about 50:1, alternatively at a mole ratio of about 2:1 to about 20:1. For example, the first and/or second mixture can have an alkane:molecular oxygen molar ratio of at least about 2:1, such as in the range of about 2:1 to about 50:1, or about 2:1 to about 20:1.

The oxidant can comprise ≥90.0% $O_2$ (molar basis, per mole of oxidant), e.g., ≥99.0% $O_2$. The oxidant can comprise (or consist essentially of, or consist of) air. Typically the oxidant comprises $O_2$ in air, or $O_2$ obtained or derived from air, e.g., by separation. Nitrogen in air, or obtained or derived from air, can be utilized as a feed mixture diluent. Optionally, the first and/or second feed mixture comprises alkane and air (such as methane and air), e.g., mixtures having an alkane-air mixture having an alkane:molecular oxygen molar ratio of at least about 2:1, e.g., ≥4:1, such as in the range of about 2:1 to about 50:1, or about 2:1 to about 20:1.

The oxidant can comprise $O_2$ in air or obtained from air. The hydrocarbon reactant can comprise ≥80% (molar basis) methane; and (iii) the catalytic hydrocarbon conversion is carried out at a methane:$O_2$ molar ratio of ≥2:1, such as from 2:1 to 50:1; or ≥3:1, such as from 3:1 to 50:1; or ≥4:1, such as from 4:1 to 50:1.

III. Oxidative Coupling Catalysts and Oxydehydrogenation Catalysts

Catalysts useful in carrying out the present reactions can be any hydrocarbon conversion catalyst effective in converting alkane (e.g., $C_{5-}$ alkane) in the hydrocarbon reactant to olefin (e.g. $C_{2+}$ olefin) through at least one of an oxidative coupling reaction and an oxydehydrogenation reaction. At least a portion of one or more of the thermal masses of the reactor comprises the catalyst. For example, the catalyst (and/or components thereof) can be arranged at one or more surfaces of the thermal mass, over which the feed components (heating fluid and hydrocarbon reactant) pass.

Particularly useful hydrocarbon conversion catalysts include oxydehydrogenation catalysts and/or oxidative coupling catalysts, such as metal oxide hydrocarbon conversion catalysts useful in oxydehydrogenation and oxidative coupling reactions. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to $C_{2+}$ olefin (e.g., ethylene).

An effective metal oxide catalyst can include at least one base metal of IUPAC Group 2, Group 3, Group 7, Group 8, Group 9, Group 14, Group 15 and the lanthanide series of metals. The metal oxide catalyst can additionally include at least one Group 1 metal. Examples of each these metals are shown in the PERIODIC CHART OF THE ELEMENTS, The Merck Index, $12^{th}$ Ed., Merck & Co., Inc., 1996 ("Periodic Table").

Examples of Group 1 metals include Li, Na, K, Rb, Cs and Fr. Li, Na, K, Rb and Cs represent more common Group 1 metals.

Examples of Group 2 metals include Be, Mg, Ca, Sr, Ba and Ra. Mg, Ca, Sr and Ba are more common Group 2 metals.

Examples of Group 3 metals include Sc, Y, La and Ac. La is an example of a particularly common Group 3 metal.

Examples of Group 7 metals include Mn and Re. Mn is an example of a particularly common Group 7 metal.

Examples of Group 8 metals include Fe, Ru and Os. Fe is an example of particularly common Group 8 metal.

Examples of Group 9 metals include Co, Rh and Ir. Co is an example of particularly common Group 9 metal.

Examples of Group 14 metals include Sn and Pb. Pb is an example of a particularly common Group 14 metal.

An example of a Group 15 metal includes Bi.

Examples of the lanthanide series of metals include Ce, Pr, Nd, Sm, Eu, Gd, Tb, Dy, Ho, Er, Tm, Yb and Lu. Sm, Gd, Ho, and Yb are more common lanthanide metals.

Specific examples of oxidative coupling catalysts include those listed in U.S. Pat. No. 6,096,934. Such catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; and lithium supported on lanthanum oxide where the lithium is present in either the hydroxide or oxide form; or any other metal or metal oxide or hydroxide catalyst promoted with a Group 1, 2, or lanthanide series element present in an oxide or hydroxide form.

U.S. Pat. No. 5,245,124 discloses an order of oxidative coupling catalysts first reported by Y. A. Amenomiya et al. in "Conversion of Methane by Oxidative Coupling," report to CANMET, Energy, Mines and Resources, Ottawa, Canada. The rating of catalysts is listed as follows: $Li/Sm_2O_3 > Na/CaO > K/CaO > LaAl_2O_3 > Sm_2O_3 > Li/CaO > PbO > Bi_2O_3 > Ho_2O_3 > Gd_2O_3 > Li/MgO > Li/CaO \sim Yb_2O_3 > Y_2O_3 Na/MgO \sim CaO > MgO$. Additives to the catalysts include Ba, Li, Sr, Pb, K, Mg, Ca, Na, and Sb.

Perovskites of the structure $A_2B_2C_3O_{10}$ are also useful as catalysts for the oxidative coupling and/or oxydehydrogenation of lower alkane to heavier hydrocarbons. A is alkali metal; B is lanthanum or a lanthanide element, for example, cerium, neodymium, samarium, praseodymium, gadolinium or dysprosium; and C is titanium. A particular example is shown in U.S. Pat. No. 5,026,945, in which the perovskite is represented by the formula $A_xLn_yTi_zO_{10}$, wherein A is one or more alkali metal; Ln is one or more of lanthanum, cerium, neodymium, samarium, praseodymium, gadolinium and dysprosium; x is about 2; y is about 2; and z is about 3.

The catalysts can be incorporated with at least one thermal mass of the reactor. In such configurations, the hydrocarbon reactant flowing through the flow-through reactor and oxygen released from the oxygen storage material of the reactor are contacted in the presence of the catalyst to convert alkane in the hydrocarbon reactant to the specified $C_2$ composition.

The catalyst is preferably arranged along with one or more of the thermal masses of the reactor to transfer heat to the hydrocarbon reactant as it passes through the flow-through reactor. For example, the catalyst (and/or components thereof) can be arranged at one or more surfaces of the thermal masses adjacent to or mixed with the oxygen storage material, and in a manner in which hydrocarbon reactant passes over or across the catalyst and released oxygen.

IV. Catalytic Reactors and Reaction Conditions

The reaction for converting alkane to $C_{2+}$ unsaturated hydrocarbon is carried out in at least one reactor. Several reactors may be combined to become a single entity that is also identified as a reactor, in that individual and combined entities may be characterized as an apparatus useful for the specified chemical conversion. Main conversion reactions in the reaction zone section of the reactor, when the feed to the reactor is comprised of methane and oxygen, are the exothermic reactions to $C_2$ products:

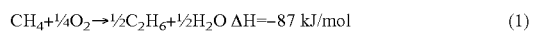

(1)

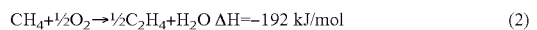

(2)

and optionally combustion, which consumes more oxygen and generates more heat:

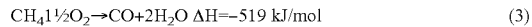

(3)

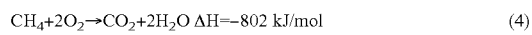

(4)

It has been found that by regulating the relative amount of hydrocarbon reactant and oxidant, reactions (1) and particularly (2) can be favored over reactions (3), and (4), and over reactions which combust one or more of the desired products. Such undesirable combustion reactions include $C_2H_x + O_2 \rightarrow CO_2 + H_2O$, such as $C_2H_4 + 3O_2 \rightarrow 2CO_2 + 2H_2O$ (−1412 kJ/mol) and $C_2H_6 + 7/2O_2 \rightarrow 2CO_2 + 3H_2O$ (−1517 kJ/mol).

The hydrocarbon conversion processes, i.e., oxidative coupling reactions and oxydehydrogenation reactions, are carried out in the presence of one or more conversion catalysts located in the reactor at temperatures and pressures effective for converting alkane to $C_{2+}$ olefins. For example, the hydrocarbon conversion process is particularly efficient when carried out at reaction zone temperatures of from 550° C. to 1100° C. Alternatively, the hydrocarbon conversion process is particularly efficient at reaction zone temperatures of from 650° C. to 900° C., or at temperatures of from 675° C. to 825° C.

Operating pressures may include a pressure of at least atmospheric pressure (zero pressure, gauge), such as ≥4 pounds per square inch gauge (psig) (28 kilo Pascals gauge (kPag)), or ≥15 psig (103 kPag), or ≥36 psig (248 kPag), or ≥44 psig (303 kPag), or ≥103 psig (710 kPag), but may be ≤300 psig (2068 kPag), or ≤163 psig (1124 kPag), or ≤150 psig (1034 kPag).

As may be appreciated, these different pressures and temperatures may be utilized together to form different combinations depending on the specific configuration of equipment.

Residence times in the reactor may be ≤20 seconds, ≤10 seconds and preferably ≤5 seconds or in the range of 0.01 seconds to 20 seconds or in the range of from 0.5 seconds to 10 seconds. For a reverse-flow reactor, the process may operate at cycle times ≥0.1 seconds, e.g., ≥0.5 seconds, such as in the range of 10 seconds to 240 seconds, in the range of 10 seconds to 120 seconds, in the range of 20 seconds to 60 seconds, or in the range of 20 seconds to 40 seconds. The term "cycle time" means the time from a first interval to the next first interval, including (i) intervening second, third, and/or fourth intervals and (ii) any dead-time between any pair of intervals. Surprisingly, it has been found that a certain range of cycle time is particularly beneficial in aspects where (i) $C_2$ selective sorbent and/or (ii) olefin-selective sorbent is located within a reverse-flow reactor and (iii) sorption and/or desorption is carried out under kinetic conditions. In those aspects, it is typically beneficial to operate at a cycle time in the range of 0.1 seconds to 60 seconds such as in the range of 0.5 seconds to 40 seconds, or 0.5 seconds to 20 seconds. Doing so is observed to decrease the amount of methane in the desorbed $C_2$ composition.

Any reactor suitable for carrying out oxidative coupling reactions and oxydehydrogenation reactions can be used, e.g., fixed-bed catalytic reactors. Examples of fixed-bed catalytic reactors include fixed-bed tubular reactors.

Reverse-flow catalytic reactors can be used, including one or more conventional reverse-flow reactors. Conventional reverse-flow reactors are typically used for converting or cracking reactions, and to execute cyclic, high temperature chemistry, such as those reactions that may be performed at temperatures higher than that which can suitably be performed in conventional steam crackers. Such reactors are described in U.S. Pat. Nos. 7,943,808, 7,491,250, 7,846,401, and 7,815,873. It has been found that when adapted as specified, reverse-flow reactors are suitable for use in certain aspects of the invention. The reactors can be physically-symmetric, e.g., about a central axis. The reactors can be adiabatic.

Reverse-flow catalytic reactor cycles typically are either symmetric or asymmetric. Asymmetric cycles are typically used to execute endothermic chemistry, and the desired endothermic chemistry is paired with a different chemistry that is exothermic (typically combustion) to provide heat of reaction for the endothermic reaction.

Regenerative, reverse-flow catalytic oxidative coupling reactors can be used to carry out the oxidative coupling and oxydehydrogenation reactions. A regenerative, reverse-flow reactor is (i) "reverse flow" in the sense that an upstream region of the reactor with respect to the average flow of the first feed mixture corresponds to the downstream region with respect to the average flow of the second feed mixture and (ii) "regenerative" in the sense that at least a portion of any heat lost (e.g., by radiation) during the e first interval is restored by heat released in the second interval (and vice versa). For example, during the first and second intervals, the reverse-flow reactor exothermically reacts the first or second mixture, as the case may be, to store heat within a defined volume (e.g., the first and/or second thermal mass). The reactors can be symmetric, asymmetric, or a combination thereof.

A variety of regenerative oxidative coupling reactors may be utilized. For example, an oxidative coupling reactor may include a housing, a plurality of flow-control means (e.g., conduits and valves), one or more insulation components (e.g., insulation bricks) and one or more process flow components (e.g., thermal mass, mixing components, etc.). The housing may be utilized to enclose an interior region and has one or more insulation components disposed adjacent to the housing. The plurality of flow control means may include one or more conduits, one or more apertures, and one or more valves that are configured to manage the flow of one or more streams into and out of the interior region from a location external to the interior region or housing. Process flow components can be configured and/or arranged to manage the flow of fluids through the interior region, wherein the one or more process flow components may include a thermal mass having different portions with each portion having different flow passages and a wetted area. In aspects where the first and/or second mixtures are combined in a reverse-flow reactor, one or more mixer or mixer-distributors can be used for the mixing.

Regenerative reverse-flow reactors may involve multiple steps repeated in sequence to form a cycle for the process. That is, the oxidative coupling process may include two or more sequential steps. The steps can include, e.g., (i) forward-flow hydrocarbon conversion step, (ii) an optional regeneration step to heat or preheat the zones containing the thermal masses, and (iii) a reverse-flow hydrocarbon conversion step. The steps may involve passing mixtures over a solid material in fixed orientation (e.g., one or more thermal masses). As part of these steps, valves may be utilized to alternate introduction of a first feed mixture and/or a second feed mixture into the interior region of the reactor.

As an example, an optional regeneration step can be used between successive forward-flow and reverse-flow hydrocarbon conversion steps. A combustion mixture of fuel, oxidant, and/or a supplemental amount of one of these reactants, can be delivered directly to a location along the flow path within the reactor (e.g., a mixing zone). The delivered reactants in the combustion mixture then exothermically react (combust) and heat the thermal mass. According to one aspect of this invention, the combustion reaction can be carried out to heat the thermal masses before, during and/or after one or more intervals of the oxidative coupling reaction. For example, a combustion reaction can be carried out to initially heat (e.g., preheat) one or more thermal masses of the reverse-flow reactor. Combustion products can then be exhausted. Following reactor regeneration, a first feed mixture can be introduced into the reactor and exposed to the heated thermal mass and catalyst to cause heating and oxidative coupling of the alkane and oxidant in the first feed mixture. The reaction products and/or unreacted first feed mixture can then be quenched as they flow through the reactor to halt the oxidative coupling catalytic reactions and/or oxydehydrogenation reactions and yield reaction products (e.g., contained in the first reaction mixture). The quenching can be accomplished, e.g., by transferring heat to a cooler region of the reactor, obviating the need for an external quench as in the conventional process. For example, the reactor can contain a cooler thermal mass (cooler than the reaction products) located downstream of the oxidative coupling and/or oxydehydrogenation reaction. In operation, the second thermal mass absorbs heat from the product mixture (e.g., the third mixture) during the first time interval, sufficient to (i) cool the product mixture to quench the reaction and (ii) impart heat to the second mixture (when the flow is reversed) during the second time interval (to preheat the feed).

The reactor may include reactor components, such as process flow components (e.g., reactor components used to manage the flow of mixtures through the reactor, one or more of the thermal masses for absorbing, storing and releasing heat, catalyst, sorbent, and/or mixing component) and insulation components (e.g., reactor components used to manage the heat transfer from the process flow within the reactor to the external surface of the reactor, such as insulation bricks, tiles or packing). The reactor components may be formed from different materials, such as refractory support materials, which can be used to support the catalyst and sorbent.

The heat generated from the conversion step may preferably be stored in a thermal mass material. The thermal mass material can be e.g., designed or adapted to facilitate storage and utilization of heat.

In certain aspects, the thermal mass is a material (e.g., a solid) that can transfer (e.g., absorb, store, and release) thermal energy over a temperature range for carrying out the reverse flow cycle, which includes the oxidative coupling reaction and any optional combustion reaction. For example, the thermal mass can be a solid material that can absorb, release, and store heat from reactants and products over a temperature range in which oxidative coupling can be carried out, including those that do so without any significant phase change. The solid material is typically one that can absorb and store heat and release the stored heat, without any significant phase change, over a temperature range in which oxidative coupling and hydrocarbon combustion are carried out. Examples of temperature ranges at which the thermal mass absorbs, stores and releases thermal energy include a range of from 50° C. to 1500° C., alternatively from 100° C. to 1500° C. or from 200° C. to 1500° C.

The thermal mass can be characterized by one or more properties. Examples of such properties include, but are not limited to, melting temperature, porosity, bulk density, thermal conductivity, thermal expansion and thermal capacity.

Melting temperatures (melting points) are reflective of the ability of the thermal mass to withstand combustion and oxidative coupling temperatures without chemical change and/or physical destruction. Thermal masses having higher melting points are preferred according to this invention. For example, the melting point of the thermal mass can be at least 1200° C., or at least 1500° C.

Porosity is a measure of the effective open pore space in the thermal mass into which heat and gasses can penetrate and eventually degrade the structure. The porosity of a thermal mass can be expressed as the average percentage of open pore space in the overall refractory volume. As an example, the thermal masses utilized in certain aspects can have a porosity of not greater than 50%, or not greater than 40%, or not greater than 30%. The porosity can be measured by an Archimedes process, e.g., mercury porosimitry.

Bulk density is a measure of the weight of a given volume of the thermal mass. Higher bulk densities, with lower porosities, can be particularly effective. As an example, the thermal masses can have a bulk density of at least 0.5 g/cm$^3$. For example, the bulk density can be from 0.5 g/cm$^3$ to 3.5 g/cm$^3$ or from 1 g/cm$^3$ to 3 g/cm$^3$.

Thermal conductivity is defined as the quantity of heat that will flow through a unit area in direction normal to the surface area in a defined time with a known temperature gradient under steady state conditions. Thermal conductivity represents a general heat flow characteristic of the thermal mass. Higher thermal conductivity thermal masses are preferred. For example, the thermal mass can have a thermal conductivity of from 0.1 W/mK to 50 W/mK or from 0.2 W/mK to 30 W/mK.

Thermal expansion of the thermal mass should not be so great such that cracking of the material occurs during operation of the reaction system. In one aspect, the thermal mass can be characterized by a thermal expansion coefficient. For example, the thermal mass can have a thermal mass coefficient of from $0.1 \times 10^{-6}$/K to $20 \times 10^{-6}$/K or from $0.2 \times 10^{-6}$/K to $15 \times 10^{-6}$/K. In this example, the thermal expansion coefficient is given as a value in a temperature range of from 25° C. to 800° C.

Thermal capacity is the ability of a material to hold heat. The thermal masses can have a higher thermal capacity, but not so high as to increase the probability of cracking at higher temperatures. For example, the thermal masses can have a thermal capacity of from 250 Jm$^3$/K to 4500 Jm$^3$/K or from 500 Jm$^3$/K to 3000 Jm$^3$/K.

Checker bricks, tiles, and monoliths may be used as to form the thermal mass components within the reactor. Such materials form a network of passages that are used by the gases in each step to transit the region containing solid material. The thermal mass may be a ceramic, which may include yttria, zirconia, alumina, and/or other refractory material capable of adsorbing, storing and transferring heat, and that are effective in withstanding temperatures within the oxidative coupling reactor.

A thermal mass can be provided, for example, in one or more beds that are useful for carrying out a chemical reaction e.g., in a uni-flow and/or reverse-flow reactor. Refractory material can be used the thermal mass components and/or locations of the sorption and reaction zones, and may be of substantially any form or shape, such as, but not limited at least one of spheres, beads, honeycomb materials, a tube, pipe, U-tube, fluid mixer, nozzle, extruded monolith, brick, tile, catalyst tray, reactor tray, tray component, valves, and/or other refractory components that are exposed to high temperature. Certain aspects include thermal mass material used in fabrication of at least one of a honeycomb monolith, a reactor bed, a reactor conduit, and a reactant mixer. As non-limiting examples, thermal mass materials can comprise one or more of glass or ceramic beads or spheres, metal beads or spheres, ceramics, ceramic or metal honeycomb materials, ceramic tubes, extruded monoliths, and the like, provided they are competent to maintain integrity, functionality, and withstand long term exposure to the relevant temperatures for the oxidative coupling and combustion reactions.

A thermal mass can include, for example, one or more conduits, channels, or passages. The term "conduit" refers to means for conducting a composition from one location to another. The term encompasses (i) elementary conducting means, such as a pipe or tube and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

The shape of the thermal mass is not restricted to any particular geometry. For example, the thermal mass can be elongated, and can have elliptical, cylindrical, and/or rectangular cross-sections, including combinations thereof. A plurality of thermal masses can be of the same shape and size, but this is not required.

Each region or zone of a thermal mass has a beginning and end represented by a plane or surface that is approximately orthogonal to net flow direction (e.g., an upstream end and a downstream end) and a region or zone has a characteristic "average zone temperature" that is an average over all locations in the zone, from the beginning of the zone to the end of the zone, and over a specified period of time. For example, the average zone temperature of a reaction zone can be determined as an average temperature from the beginning of the reaction zone to the end, which is determined over the time period reactants are flowing through the zone. To compare average zone temperatures, such as the average zone temperature of a reaction zone to a sorption zone, the average temperatures from the beginning of the zones to the end of the zones are preferably determined over comparable time periods in which fluids flow through the respective zones. Although the thermal mass can be in thermal equilibrium at a substantially constant temperature over all its locations, this is not required, and in certain aspects a thermal mass exhibits temperature profile indicating a progression or decrease in temperature across the thermal mass. This can be the case when there is heat exchange between fluid flowing through the thermal mass and the thermal mass itself. There need not be any physical manifestation within the thermal mass of the zone's beginning or end. It may simply be a mathematical construct defining region within an otherwise homogenous thermal mass. Within any zone, the thermal mass contents can be characterized in terms of volumetric wetted area ($a_v$). If the zone is homogenous in contents, $a_v$ will be constant throughout the zone. If the zone is inhomogeneous, then $a_v$ should be taken as a volume average over the zone.

One or more of the thermal masses can include separate passages through reactor components to manage the flow of hydrocarbon components and or oxidant through the thermal mass. Preferably, each thermal mass includes separate passages. The separate flow passages in the thermal mass can further comprise flow barriers that effectively function as walls to lessen or prevent cross flow or mixing of fluids (e.g., reactants, oxidants, and/or products) between passages, except in the desired regions of the reactor. Each thermal mass preferably includes multiple passages, which may preferably be in parallel flow arrangement e.g., a channeled thermal mass that is comprised of one or more honeycomb monoliths. Preferred honeycomb monoliths are structures that comprise many (e.g., a plurality, meaning more than one) gas flow passages, arranged in parallel fashion with walls serving to separate each passage. A thermal mass can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as thermal mass because they provide high heat transfer capacity with lessened pressure drop.

The thermal mass may include (i) a first portion comprising a first plurality of flow passages and having a first wetted area $a_{v1}$; and (ii) a second portion comprising a second plurality of flow passages and having a second wetted area $a_{v2}$, wherein (i) $a_{v1} \neq a_{v2}$ and (ii) $a_{v2}$ is different from $a_{v1}$ by at least 25%. The difference percentage for $a_v$, as used herein, is defined to be based on the higher of the two wetted areas. For example, if $a_{v1} \geq a_{v2}$, then the percent difference between $a_{v1}$ and $a_{v2}$ is $100*(a_{v1}-a_{v2})/a_{v1}$.

V. $C_2$ Selective Sorbent

At least a portion of one or more of the thermal masses of the flow-through reactor can optionally include a $C_2$ selective sorbent. For example, the $C_2$ selective sorbent can be included as one or more portions or sections of the thermal mass, over which the gasses pass. For example, the $C_2$ selective sorbent can be arranged at a surface of one or more sections of the thermal mass, over which reaction conversion products pass.

In an alternative optional aspect, the $C_2$ selective sorbent can be included in external arrangement with the reactor. For example, the $C_2$ selective sorbent can be included in a $C_2$ selective sorption system, configured in fluid communication with an exit aperture of the reactor for receiving at least a portion of the catalytically converted reaction mixture.

Selective removal of one or more desired $C_2$ compositions can be carried out without having to rely on cryogenic processes by using a $C_2$ selective sorbent. The $C_2$ selective sorbent is preferably configured to selectively remove or extract at least one $C_2$ compound from a gas stream as the gas stream flows past or through the $C_2$ selective sorbent.

As used herein, a sorbent is considered a generic term, which includes "absorbent" and "adsorbent." An absorbent is a material that absorbs or incorporates a substance into the body of the absorbent material, which can also be referred to as absorption. For example, an absorbent can be used to absorb or attract or remove or extract a substance from another substance or from a mixture of substances. An adsorbent is a material that adsorbs or attracts a substance to the surface of the sorbent material, which can also be referred to as adsorption. For example, an adsorbent can be used to adsorb or attract or remove or extract a substance from another substance or from a mixture of substances.

The $C_2$ selective sorbent is effective in removing or selectively sorbing one or more $C_2$ compounds from a hydrocarbon-containing composition, particularly the specified $C_2$ composition. Alternatively or in addition, the sorbent can be effective in removing or selectively sorbing one or more olefin compounds from a hydrocarbon-containing composition. In particular, the sorbent can be effective in selectively sorbing or removing at least one compound selected from the group consisting of ethane, ethylene and acetylene. In some cases, the sorbent can selective for one of ethane, ethylene and acetylene. For example, a sorbent selective for ethylene over ethane and acetylene can be used, such as one or more of the olefin-selective sorbents. Alternatively, the sorbent can selective for two of ethane, ethylene and acetylene. Alternatively, the sorbent can selective for each of ethane, ethylene and acetylene.

In cases in which a first sorbent is used to sorb at least two of ethane, ethylene and acetylene, or each of ethane, ethylene and acetylene, a second sorbent, can be used. The second sorbent typically comprises at least one olefin-selective sorbent, which can be used in a subsequent step to separate one of the $C_2$ compounds sorbed by the first sorbent. For example, in a first step a sorbent selective for selectively separating ethane and ethylene from methane can be used (a $C_2$ selective sorbent), followed by a second sorption step in which a sorbent selective for separating ethylene can be used (an olefin-selective sorbent).

$C_2$ selective sorbents typically comprise at least one solid composition that is effective in selectively removing at least one $C_2$ component from a gas stream containing one or more $C_2$ compositions as the gas stream passes across or through the sorbent. Such solid compositions can include molecular sieve, e.g., one or more (i) ordered mesoporous material, (ii) ordered microporous material, (iii) zeolite, aluminophosphate, etc. The $C_2$ selective sorbent typically has a surface area of $\geq 50$ m$^2$/g, e.g., $\geq 100$ m$^2$/g. The particular type of sorbent to be used can depend on the particular nature of the gases to be separated.

A kinetic separation separates by differences in diffusion and/or sorption rates through the sorbent; the differences in diffusion rates may be caused by chemoselectivity, shape selectivity or a combination of both. Kinetic separations differ from thermodynamic separations. In a thermodynamic separation, sufficient time is allowed for the gases to equilibrate with the sorbent. However, in a kinetic separation, equilibrium is not achieved (e.g., by operating at higher rates per volume of sorbent, or by shortening the bed). Moreover, kinetic adsorbents discriminate amongst species by significant differences in the speed of diffusion and/or adsorption of ethylene compared to ethane, regardless of the respective species' equilibrium capacities/selectivities. For example, in a situation in which ethylene is the desired sorbate, a sorbent can be used that is particularly selective for ethylene at a pre-determined temperature. In certain aspects, at least one sorbent is used which is selective for removing ethylene from a gas stream under kinetic sorption conditions at a temperature region within or below the desired temperature range of the oxidative coupling reaction.

In certain aspects, the adsorbent for removing at least one of the $C_2$ compositions is comprised of a $C_2$ selective sorbent having a selectivity for sorbing the desired $C_2$ composition over sorbing of methane that is greater than 5. Alternatively, the adsorbent for removing at least one of the $C_2$ compositions is comprised of a $C_2$ selective adsorption material having an adsorptive loading ratio for the desired $C_2$ composition over methane of at least 10, or at least 15, or at least 20. Examples of such materials include zeolitic imidazolate framework materials, such as ZIF-7, ZIF-9 and ZIF-1 as described in greater detail in U.S. Pat. No. 8,192,709.

The adsorptive loading ratio is a property for a specific adsorbate-adsorbent pair, at given conditions of pressure and temperature. This ratio is defined herein as a unitless quantity that is equal to the adsorption loading (in mmole/g) for the first component divided by the adsorption loading (in mmole/g) for the second component for a specific adsorbent material at a specific pressure and temperature. The adsorption loading for the desired $C_2$ composition on a particular adsorbent can be determined as described in U.S. Pat. No. 8,192,709, which is incorporated herein by reference.

In certain aspects, the $C_2$ selective sorbent has a $C_2$:methane selectivity >1. For example, the $C_2$ selective sorbent can retain >50% [ethylene+ethane] and <50% methane; such as a $C_2$:methane selectivity >5 (i.e., retains >83% [ethylene+ethane]); or a $C_2$:methane selectivity >99 (i.e., retains >99% ethylene+ethane); or a $C_2$:methane selectivity >999 (i.e., retains >99.9% [ethylene+ethane]); or a $C_2$:methane selectivity >9999 (i.e., retains >99.99% [ethylene+ethane]).

The $C_2$ selective sorbent can be an olefin-selective sorbent, e.g., a sorbent having an ethylene:ethane selectivity >1 (i.e., retains >50% ethylene, ≤50% ethane). For example, the $C_2$ selective sorbent can have an ethylene:ethane selectivity >5 (i.e., retains >83% ethylene); such as an ethylene:ethane selectivity >99 (i.e., retains >99% ethylene); or >999 (i.e., retains >99.9% ethylene); or an ethylene:ethane selectivity >9999 (i.e., retains >99.99% ethylene).

Olefin-selective sorbents include porous materials having a high surface area, which have been treated with transition metal species capable of π-complexation with olefins. In particular, the double bond of the olefin can form π-complexes with certain transition metals, bringing about a difference in adsorption affinity between olefin and paraffin compositions. The π-complex is formed by the donation of π-electrons of the olefin to the empty σ-orbital of a transition metal and the back-donation of d-electrons of the transition metal to the π*-orbitals of the olefin. Optionally, the olefin-selective sorbents have an electron affinity ≥1.0 ev, e.g., ≥5.0 ev, such as ≥7.0 ev. Metals satisfying one or both of these criteria are those from groups IA through VIIIA, IB and IIB on the periodic table and their combinations. These metals may be extra-framework (e.g., ion exchanged or as metal clusters) or may be part of the framework of the adsorbent (by isomorphic substitution).

Group 9 transition metals are examples of transition metals that have a relatively high degree of π-complexation with olefins. Specific examples of Group 9 transition metals include copper and silver, particularly in their salt form. Such sorbents are described in U.S. Pat. No. 4,917,711, which describes the use of supports such as zeolite 4A, zeolite X, zeolite Y, alumina and silica, each treated with a copper salt, to selectively remove carbon monoxide and/or olefins from a gaseous mixture containing saturated hydrocarbons (i.e. paraffins) such as ethane and propane.

In certain aspects, the olefin-selective sorbent has shape-selectivity. For example, the olefin-selective sorbent can comprise molecular sieve (e.g., as a substrate material), the molecular sieve having an average pore size that selectively excludes ethane from entering the pores of the sorbent, but allows ethylene to enter. Certain olefin-selective sorbents have an average pore size of not greater than 4.4 angstroms, or not greater than 4.3 angstroms, or not greater than 4.2 angstroms.

In particular aspects, the olefin-selective sorbent comprises a small pore molecular sieve, e.g., a small pore molecular sieve having at least one set of pores of substantially uniform size extending through the molecular sieve, wherein geometric mean of the cross-sectional dimensions of each of the pores is less than or equal to 4.4 Å. Suitable molecular sieves comprise zeolites, silico-alumino-phosphates (SAPOs), alumino-phosphates (AlPOs), metal organic frameworks (MOFs), zeolite imidazoline frameworks (ZIFs) and polyaromatic frameworks (PAFs). Examples of suitable molecular sieves include materials having the framework types CHA, WEN, ABW, PHI, IHO, GIS, LOV, MON, AEI, POU, ATV, MFS, DDR, ATN, CHI, FER, LTA, LEV, ROG, DAC, ERI and ATT (see "Atlas of Zeolite Framework Types", eds. Ch. Baerlocher, L. B. McCusker, D. H. Olson, Elsevier, Sixth Revised Edition, 2007, which is hereby incorporated by reference). For example, ATT framework type molecular sieves have two sets pores, each defined by 8-ring channels, extending through the molecular sieve, wherein the pores of one set having cross-sectional dimensions of 4.2 Å×4.6 Å (geometric mean 4.4 Å) and the pores of the other set having cross-sectional dimensions of 3.8 Å×3.8 Å (geometric mean 3.8 Å). Thus, the geometric mean of the cross-sectional dimensions of all the pores defined by these 8-ring channels in ATT material is less than or equal to 4.4 Å.

An example of a sorbent useful sorbents is provided in U.S. Pat. Nos. 6,867,166 and 6,423,881, which describe the use of copper salts and silver compounds supported alternatively on silica, alumina, MCM-41 zeolite, 4A zeolite, carbon molecular sieves, polymers such as Amerberlyst-35 resin, and alumina. The silver and copper supported sorbents are effective in selectively sorbing olefins from gaseous mixtures containing olefins and paraffins. Both kinetic and thermodynamic separation behavior is disclosed.

Clay based sorbents can also be used. Examples are described by Choudary et al. in the *Ind. Eng. Chem. Res.* 2002, v 41, p. 2728. As one example, $Ag^+$ impregnated clay sorbents are selective for olefin uptake from a gaseous olefin/paraffin mixture. The sorbent is evaluated for ethylene separation from ethane, with over 85% recovery and at over 99% purity.

Another useful sorbent is described in *Chemical Engineering Research and Design*, 2006, 84(A5) p. 350, by Van Miltenburg et al., in which $Cu^+$ was used to modify Faujasite zeolites. The modified zeolites are useful sorbents for the separation of ethylene from ethylene/ethane mixtures. The use of similarly modified Faujasite zeolites in a highly selective PSA process that separates carbon monoxide and/or olefins from a mixture that also contained paraffins is also reported in U.S. Pat. No. 4,717,398 assigned to BP.

Copper modified 4 A zeolites, as described in U.S. Pat. Nos. 5,744,687; 6,200,366 and 5,365,011 assigned to BOC, are used to separate ethylene and propylene from ethane and propane respectively. Zeolites such as zeolite 5A and zeolite 13× are also used in the formation of copper modified sorbents.

Aluminophosphates, such as described in U.S. Pat. No. 6,293,999 assigned to UOP, are used to separate propylene from propane. The aluminophosphate can be a small pore molecular sieve, such as "AlPO-14". Analogous zeolite sorbents can also be used in the invention.

Metal organic frameworks are also useful in selectively separating olefin from gas mixtures, with Fe-organic frameworks being particularly useful. For example, a metal-organic framework having a redox-active metal center (e.g., Fe2 (dobdc)), such as described in U.S. Patent Publication No. 2013/0053585, is effective in separating olefin/paraffin mixtures such as ethylene/ethane and propylene/propane.

VI. $C_2$ Selective Sorption Process and System

The $C_2$ selective sorbent has an ultimate capacity for sorbing the sorbate (e.g., the $C_2$ composition) from the reaction mixture produced by the oxidative coupling reactions and/or oxydehydrogenation reactions. Exposing the reaction mixture to at least one $C_2$ selective sorbent results in the selective sorption of at least a portion of the reaction mixture's $C_2$ composition, producing a $C_2$ lean mixture.

During the sorption process, the appearance of an increased amount of the $C_2$ composition in the $C_2$ lean mixture can be an indication that the $C_2$ selective sorbent is approaching the ultimate capacity. The appearance of an increased amount of the $C_2$ composition in the $C_2$ lean mixture can also be referred as "break-through." At a predetermined time of break-through, the passing of the reaction mixture to the $C_2$ selective sorbent can be lessened or discontinued, and the sorbed olefin can be desorbed from the $C_2$ selective sorbent.

Typically, the $C_2$ composition is desorbed from the one $C_2$ selective sorbent in order to (i) regenerate the one $C_2$ selective sorbent (to restore capacity for sorbing the reaction mixture's $C_2$ composition) and (ii) to recover the desorbed $C_2$ composition. Conventional sorbent regeneration conditions are suitable. Desorption be carried out by a reduction in temperature, pressure or both.

Optionally, a sweep fluid can be used to assist in desorbing the $C_2$ composition. Typical sweep fluids include relatively inert liquids and vapors, especially those which are relatively easy to separate from the desorbed $C_2$ composition. Steam and/or molecular nitrogen are suitable sweep fluids. $C_2$ unsaturates can be separated from the desorbed $C_2$ composition, e.g., for storage and/or further processing, such as the polymerization of ethylene obtained from the $C_2$ composition.

Selective separation or sorption of the sorbate, i.e., sorption of the $C_2$ composition, is carried out at a temperature in a range below that of the oxidative coupling reaction. For example, the sorbent can be located in a sorption region or zone in which the sorption zone is downstream of the reaction zone, and the sorption zone is at an average zone temperature that is less than that of the average zone temperature within the reaction zone. As an example, the sorption zone can be at an average zone temperature of at least 50° C., or at least 100° C., or at least 200° C., or at least 400° C. lower than the average zone temperature within the reaction zone. Sorption can be carried out at a temperature range of from 50° C. to 400° C., such that is greater than the pressure range of the reaction zone. As a practical matter, the pressure of the sorption zone can be ≥100 psig (489 kPag), such as from 100 psig (489 kPa) to 500 psig (3447 kPag).

Selective separation of the $C_2$ composition, such as from the reaction mixture and/or the $CO_2$ lean reaction mixture, can be carried out at a temperature of at least 50° C. less than that of the average zone temperature within the reaction zone.

Desorption of the sorbate can be carried out at an average sorption zone temperature lower than the average zone temperature of the reaction zone, e.g., at a temperature that is from 50° C. to 400° C. lower than the average zone temperature of the reaction zone, such as 100° C. to 300° C. lower.

Desorption of the sorbate can also be carried out at an average temperature greater than that used for sorption of the sorbate. For example, desorption of the sorbate can also be carried out at an average temperature of at least 4° C., or at least 5° C., or at least 6° C. above that used for sorption of the sorbate. In certain aspects, desorption of the sorbate is carried out at 4° C. to 200° C. above that used for sorption of the sorbate.

In certain aspects, desorption of the sorbate can be carried out at an average pressure below that used for sorption of the sorbate. For example, desorption of the sorbate can be carried out at an average pressure of from >0 psia (0 kPa) and from 1 psia (6.9 kPa) to 485 psia (3344 kPa) below that used for sorption of the sorbate.

The specified sorbents can be utilized in a swing adsorption process or system. The general terms "swing adsorption process" and "swing adsorption system" as used herein shall be taken to include Pressure Swing Adsorption ("PSA"), Temperature Swing Adsorption ("TSA"), Pressure Purge Displacement Processes ("PPSA"), Rapid Cycle Pressure Swing Adsorption ("RCPSA"), Rapid Cycle Temperature Swing Adsorption ("RCTSA"), Rapid Cycle Pressure Purge Swing Absorption ("RCPPSA") as well as combinations of these swing adsorption processes. Alternatively, a simulated moving-bed chromatography separation may be used. The stream to be separated is typically fed to the process in a substantially gaseous state.

The composition desorbed from a $C_2$ selective sorbent (the "desorb composition") typically comprises <50% (molar) methane and ≥50% (molar) of the sorbed $C_2$ composition, e.g., ≥75% such as ≥90%, or ≥95%, or ≥99%. The desorb composition from an Olefin-selective sorbent typically comprises <50% (molar) alkane (e.g., ethane) and ≥50% (molar) of olefin (e.g., ethylene), such as ≥75%, or ≥90%, or ≥99%.

VII. Recovering a $C_2$ Composition Produced in a Tubular Reverse-Flow Catalytic Reactor Oxidative coupling and oxydehydrogenation can be effectively and efficiently carried out in reverse-flow catalytic reactors to produce reaction mixtures containing relatively high quantities of $C_2$ compositions. Removing and/or recovering the reaction mixtures' $C_2$ composition can be carried out highly effectively and efficiently by configuring $C_2$ selective sorbent systems in particular fluid communication process flows with the reverse-flow reactor.

Typical reverse-flow catalytic reactors comprise elongated tubes having first and second ends. At least one aperture (a first aperture) is typically located proximate to the first end for providing for the flow of fluids into and out of the reactor. At least one aperture (a second aperture) is typically located proximate to the second end, for providing for the flow of fluids into and out of the reactor.

In certain aspects, the reverse-flow reactor further comprises first and second thermal masses. The first thermal mass is typically located in a first internal region of the reactor proximate to the first end. A second thermal mass is typically located in a second internal region of the reactor proximate to the second end. The first and thermal masses are capable of storing and releasing heat to the reactor and to fluids conducted into, out of, and through the reactor.

The reverse-flow reactor further comprises hydrocarbon conversion catalyst. In certain aspects, the catalyst can be located in a third internal region of the reactor, the third region being located between the first and second regions. The regions of the reverse-flow reactor are optionally non-overlapping regions. For example, ≥50.0 wt. % of the hydrocarbon conversion catalyst, based on total weight of the hydrocarbon conversion catalyst, can be located in a zone between the first and second regions. The first and second regions can be separate, non-overlapping regions of the reverse-flow reactor. At least a portion of the hydrocarbon conversion catalyst can be located in and/or on one or more of the thermal masses.

In certain aspects, (i) ≥50.0 wt. % of the first thermal mass, based on total weight of the first thermal mass, can be located in a first region of the reverse-flow reactor, (ii) ≥50.0 wt. % of the second thermal mass, based on total weight of the second thermal mass, can be located in a second region of the reverse-flow reactor, and (iii) ≥50 wt. % of the hydrocarbon conversion catalyst, based on total of the hydrocarbon conversion catalyst, can be located in a third region of the reverse-flow reactor, the third region being located between the first and second regions.

The reverse-flow catalytic reactor is typically operated in "flows." For example, a first flow (or "forward flow") can be carried out in which a first feed mixture (e.g., a first hydrocarbon reactant and oxidant) enters the reactor proximate to the first aperture, with one or more components of the first reaction mixture exiting the reactor proximate to the second aperture. In a second flow ("reverse flow"), a second feed mixture (e.g., a second hydrocarbon reactant and oxidant) enters the reactor proximate to the second aperture, with one or more components of the second reaction mixture exiting the reactor proximate to the first aperture.

Flows can be established for separating (i.e., sorbing) and recovering $C_2$ compositions from the first and second reaction mixtures. For example, the first and/or second reaction mixtures can be conducted away from the reverse-flow reactor and passed to at least one sorption stage to sorb the first and/or reaction mixture's $C_2$ composition using an olefin-selective sorbent. The temperature and/or pressure of the olefin-selective sorbent can be adjusted to desorb and recover the desired $C_2$ composition.

As an example of a reverse-flow catalytic reactor system, a first hydrocarbon reactant and first oxidant can be provided to the reverse-flow catalytic reactor when the process is operated in the forward direction. A second hydrocarbon reactant and second oxidant can be provided to the reverse-flow reactor when the process is operated in the reverse direction. Reactant and oxidant can be mixed upstream of the reverse-flow reactor. For example, a first feed mixture can be provided to the reactor when operating in the forward direction, the first feed mixture comprising the specified first hydrocarbon and the specified oxidant. A second feed mixture can be provided to the reactor when operating in the reverse direction, the second mixture comprising a second hydrocarbon reactant and second oxidant. The second hydrocarbon reactant can be selected from among the same compositions as those specified for the first hydrocarbon reactant. The second oxidant can be selected from among the same compositions as those specified for the first oxidant. Optionally, the first hydrocarbon reactant has substantially the same composition as the second hydrocarbon reactant and (ii) the first oxidant has substantially the same composition as the second oxidant. Optionally, the second feed mixture can be selected from among the same compositions as the first feed mixture. Optionally, the second feed mixture has substantially the same composition as the first feed mixture.

During a first time interval, the first feed mixture can be passed into and through the reverse-flow catalytic reactor in the forward-flow direction. The first feed mixture reacts (exothermally) in the reactor in the presence of a first hydrocarbon conversion catalyst. Heat can be transferred from the first thermal mass, which can be previously heated, to the first feed mixture (or one or more components thereof prior to mixing) to produce a heated first feed mixture. At least a portion of the heated first feed mixture's alkane is catalytically converted in the presence of at least a portion of the heated first feed mixture's oxidant and in the presence of the first hydrocarbon conversion catalyst to produce a first reaction mixture. The first reaction mixture can comprise (A) $C_2$ composition produced by the alkane conversion and (B) any unconverted first feed mixture. Heat can be transferred from the first reaction mixture to the second thermal mass, to produce a cooled first reaction mixture.

During a second time interval, the second feed mixture can be passed to the reverse-flow reactor in the reverse-flow direction. Heat can be transferred from the second thermal mass to the second feed mixture (or to one or more components thereof prior to mixing) to produce a heated second feed mixture. The second thermal mass can be heated before the second time interval, e.g., during the first interval, as a result of the heat transfer from the reaction mixture to the second thermal mass. At least a portion of the heated second feed mixture's alkane can be catalytically converted in the presence of at least a portion of the heated second feed mixture's alkane and a second hydrocarbon conversion catalyst to produce a second reaction mixture. The second reaction mixture can comprise (A) $C_2$ composition produced by the alkane conversion and (B) any unreacted second feed mixture. Heat can be transferred from the second reaction mixture to the first thermal mass to re-heat the first thermal mass and produce a cooled second reaction mixture.

The cooled first and/or second reaction mixture can be conducted away from the reverse-flow reactor to an olefin sorption system having at least one separation stage to separate and/or recover the first and/or reaction mixture's $C_2$ composition. For example, the first and/or second reaction mixture can be conducted away from the reverse-flow reactor to at least one separation stage in fluid communication with the reverse-flow reactor. The separation stage contains at least one $C_2$ selective sorbent for sorbing at least a portion of the cooled first reaction mixture's $C_2$ composition. For example, the cooled first reaction mixture can be optionally treated to remove $CO_2$ and/or water and passed to at least one adsorber unit of a swing adsorption system to adsorb the reaction mixture's $C_2$ composition. At the adsorber unit's sorption capacity, passage of the reaction mixture to the adsorber unit of the swing adsorber system can be lessened or discontinued, and the temperature and/or pressure of the unit can be adjusted to desorb at least a portion of the sorbed $C_2$ composition, at least partially regenerating the $C_2$ selective sorbent. A sweep fluid can be optionally used to enhance desorption of the sorbed $C_2$ composition for the adsorber unit.

VIII. Selective Removal of $CO_2$ and $H_2O$

Desired recovery and/or separation of a desired $C_2$ composition can be carried out through little if any reliance on cryogenic separation processes according to this invention. In certain aspects, the non-cryogenic process can be carried out by including a step of selectively removing from the reaction mixture at least a portion of the $CO_2$ produced during the alkane conversion to produce a $CO_2$ lean reaction mixture. The $CO_2$ lean reaction mixture can be comprised of at least a portion of the $C_2$ composition produced by the alkane conversion and at least a portion of the unconverted methane, with the $CO_2$ lean reaction mixture having a $CO_2$ content less than that of the reaction mixture.

Typically, the $C_2$ composition comprises ≥90% (molar basis, per mole of $C_2$ composition) of one or more of (i) ethane, (ii) ethylene, and (iii) acetylene, e.g., ≥95%, such as ≥99%. For example, the $C_2$ composition can comprise ≥90% of (i) ethane and (ii) ethylene, such as ≥95%, or ≥99%. The $C_2$ composition can be one that predominantly comprises $C_2$ unsaturates, e.g., ≥50% of (i) ethylene and/or (ii) acetylene, such as ≥75% ethylene, or ≥90% ethylene, or ≥99% ethylene, with the balance comprising ethane, e.g., <50% ethane, such as ≤25%, or ≤10%, or ≤1% ethane. One suitable $C_2$ composition comprises 50% to 99% ethylene, with the balance comprising ethane, e.g., 75% to 99% ethylene or 90% to 99% ethylene.

The $C_2$ composition separated from the reaction mixture can be separated from the $CO_2$ lean reaction mixture. A $CO_2$ lean reaction mixture can comprise hydrocarbon produced from the conversion reaction, and less $CO_2$ than the reaction mixture itself. The $CO_2$ lean reaction mixture can have a $CO_2$ content of not greater than 5 mol %, or of not greater than 3 mol %, based on total volume of the $CO_2$ lean reaction mixture.

Selective removal or separation of the $CO_2$ from the reaction mixture can be carried out by any suitable process. For example, separation can be carried out by one or more of distillation, membrane separation and sorption using an appropriate sorbent, where the term "sorbent" means a material that sorbs or attracts a substance from another substance. Sorption can be by absorption (using chemical or physical solvents) or adsorption. For example, selective separation of the $CO_2$ from the reaction mixture can be carried out by reaction with an appropriate base. Amine-based chemical treatments can be used. Particular examples of amine-based treatments include alkanolamines. Alkanolamines include primary amines such as monoethanol amine and digylcolamine; secondary amines such as diethanol amine and diidopropyl amine; and tertiary amines such as triethanol amine and methyldiethanol amine.

Although amine-based solvents can be considered chemical solvents, physical-type solvents can also be used to selectively separate $CO_2$ from the reaction mixture by physical absorption. Physical-type absorbents allow a gas to permeate a solid or liquid under one set of conditions, and desorb under others. The rate of absorption or desorption is temperature and pressure dependent. Smaller differences in conditions can require less energy, although more absorbent may be needed to capture $CO_2$ at an equivalent rate.

Absorption in physical solvent systems can occur at high partial pressure of $CO_2$ and low temperatures. The solvents can then regenerated by heating, pressure reduction, or a combination of both.

Other methods of $CO_2$ removal may include physical solvent scrubbing of $CO_2$ with a glycol-based solvent. Methanol and glycerol are other examples of physical solvents that can be used for removing $CO_2$.

$CO_2$ can also be selectively separated for removed from the reaction mixture by physical adsorption. Physical adsorption relies on the affinity of $CO_2$ to the surface of a material under certain conditions without forming a chemical bond. Adsorbents can separate $CO_2$ from a stream by preferentially attracting it to the material surface at high pressures through weak interactions such as van der Waals forces. During capture, the chemical potential of the adsorbed $CO_2$ is lower than the chemical potential of $CO_2$ in the gas mixture.

Regenerable adsorbents can also be used to separate the $CO_2$. Regenerable adsorbents have the ability to reverse the chemical potential of the adsorbed phase upon changing the conditions to remove the $CO_2$. This can be accomplished by changing pressure and/or temperature conditions or stripping with an easily separable gas such as steam. Swing adsorption systems (pressure and/or temperature swing absorption) can be used.

Examples of adsorbents useful for selectively separating $CO_2$ include, but are not limited to, activated carbon and molecular sieves. Examples of molecular sieves include, but are not limited to, zeolites and hydrotalcites.

Membrane systems can also be used to separate $CO_2$. Membrane systems include relatively thin barriers that allow selective permeation of certain gases, allowing one component in a gas stream to pass through faster than the others. Examples of membranes that can be used to selectively adsorb $CO_2$ from the reaction mixture include polymeric membranes, inorganic microporous membranes, and palladium membranes. Polymeric membranes include cellulose acetate, polysulfone, and polyimide. Inorganic membranes can be particularly beneficial for withstanding high temperatures. Membrane separation combined with solvent separation can be highly effective.

Water removal can be accomplished by any suitable means. For example, water can be relatively easily removed by condensing the water, while leaving lower boiling point components of the reaction mixture in vapor phase. Examples of such processes include flash separation and/or distillation.

IX. Examples

Example 1 (with Reference to FIG. 1)

FIG. 1 depicts a generalized system for selectively removing the specified $C_2$ composition according to certain aspects of the invention. Hydrocarbon conversion reactor 100 contains the specified hydrocarbon conversion catalyst, namely one having oxidative coupling and/or oxydehydrogenation functionality. A hydrocarbon reactant containing methane ($CH_4$) is introduced into the hydrocarbon conversion reactor 100 via a line 102, and oxidant containing molecular oxygen ($O_2$) is introduced via a line 104. At least a portion of the methane is catalytically converted to a reaction mixture comprising (i) a $C_{2+}$ composition, including at least ethane and ethylene, and (ii) $CO_2$ and/or water, and (iii) any unreacted methane. The reaction mixture exits the reactor via a line 106 and is sent to a first separation unit 108 for removing at least a portion of the $CO_2$ and water. A $CO_2$ lean and water lean stream exits the first separation unit via a line 110 and is sent to a second unit 112. $CO_2$ and water removed from the reaction mixture in the first separation unit 108 can be later conducted away the first separation unit 108. Typically, the $CO_2$ is reacted, with the reaction products being conducted away from stage 108.

At least a portion of the $C_2$ composition (e.g., ethane and/or ethylene) present in the $CO_2$ lean and water lean stream is selectively adsorbed by at least one $C_2$ selective sorbent in second separation unit 112, producing a methane rich stream 116. In addition, a purge stream 118 may be removed from unit 112. The methane rich stream is shown as being recycled via a line 116 back to the hydrocarbon conversion reactor 100 for re-processing, although at least a portion of the methane stream can be used for further processing in alternate processes. The sorbed $C_2$ composition can be desorbed by lessening or discontinuing flow of the hydrocarbon reaction mixture through line 110 to the second separation unit 112. Temperature and/or pressure of unit 112 can be adjusted to desorb at least a portion of the sorbed $C_2$ composition, and the desorbed $C_2$ composition can be recovered by way of line 114. A sweep fluid can be flowed through a line 120 to the second selective sorption unit 112 to enhance desorption and recovery of the $C_2$ composition.

Figure 2:
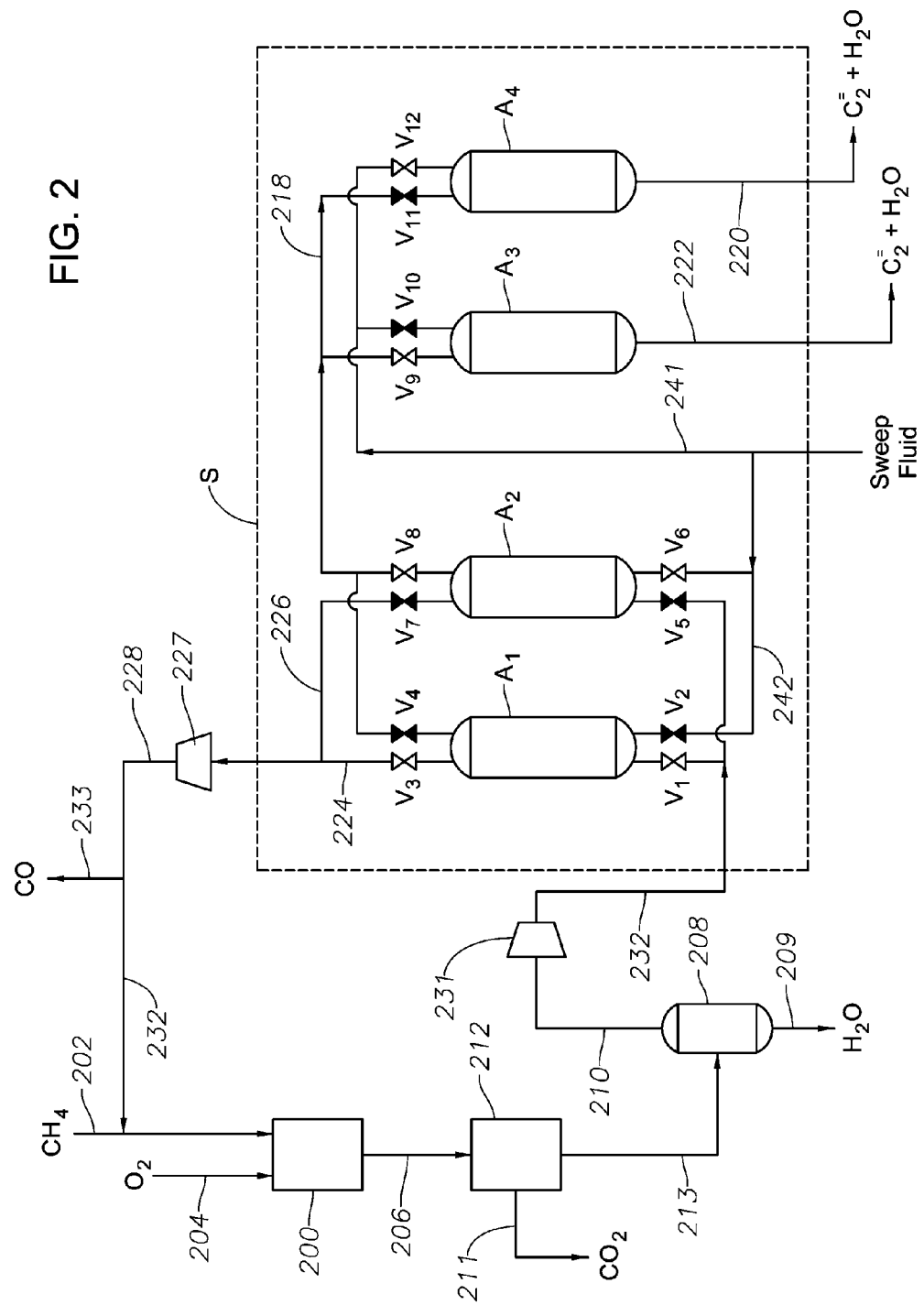
FIG. 2 is a simplified diagrammatic illustration of a more particular system for selectively removing a $C_2$ composition according to certain aspects of the invention.

Example 2 (with Reference to FIG. 2)

FIG. 2 depicts another generalized system for selectively removing a $C_2$ composition according to certain aspects of the invention. Hydrocarbon conversion reactor 200 contains catalyst the specified hydrocarbon conversion catalyst. A hydrocarbon reactant containing methane ($CH_4$) is introduced into the hydrocarbon conversion reactor 200 via a line 202, and oxidant containing molecular oxygen ($O_2$) is introduced via a line 204. At least a portion of the methane is catalytically converted to a reaction mixture comprised of $C_{2+}$ compositions, including at least ethane and ethylene, as well as $CO_2$ and water, and further includes any unreacted methane. The reaction mixture exits the reactor via a line 206, and is sent to a $CO_2$ separation unit 212 to selectively remove at least a portion of the $CO_2$ via a line 211 (typically in the form of products of a $CO_2$ conversion reaction). A $CO_2$ lean stream exits the $CO_2$ separation unit via a line 213 and is sent to a water separation unit 208 to selectively remove at least a portion of the water via a line 209. A $CO_2$ lean and water lean stream exits the water separation unit 208 via a line 210 and is sent to an optional first compressor 231. The compressor can be used to boost the pressure of the $CO_2$ lean and water lean stream in line 210 to a pressure of ≥100 psig (489 kPag) if needed, with the pressurized $CO_2$ lean and water lean stream being passed by a line 232 to a $C_2$ selective sorption system S.

The $C_2$ selective sorption system S in FIG. 2 is a representative aspect of a swing sorption system, comprising sorbent units A1 and A2 containing $C_2$ selective sorbent for sorbing and recovering $C_2$ compositions. Units A3 and A4 contain olefin-selective sorbent. Sorbent units A1 and A3 are shown in sorption mode, with valves V1, V3, V6, V8, V9 and V12 being in the open position. The sorbent units A2 and A4 are shown in desorption mode, with valves V2, V4, V5, V7, V10 and V11 being in the closed position. In this desorption mode, no fluid is flowed through line 226, or from A1 to line 218. Flow through all other lines is as follows.

As shown in FIG. 2, the $CO_2$ lean and water lean stream is sent to sorbent unit A1, which is at a temperature lower than the hydrocarbon conversion reactor 200 and ≥50° C. As the stream passes through the sorbent unit A1, $C_2$ composition (e.g., ethane and ethylene) is adsorbed by the sorbent. Unreacted methane and other reaction components such as CO flow through the sorbent unit A1, exiting by way of open valve V3 and line 224 as a methane rich stream. In the mode of operation shown in FIG. 2, the methane rich stream is sent to a compressor 227, which may be optional. For example, only one of compressor 231 and compressor 227 may be utilized to maintain the desired operating pressures. However, both compressor 231 and compressor 227 can be utilized if desired.

The methane rich stream exits compressor 227 via line 228. In recycle mode, the methane rich stream can be recycled to hydrocarbon conversion reactor 200 via line 232. At times, the methane rich stream can build in CO content. In such case, the methane rich stream can be purged via a line 223 and further processed such as by flaring or further oxidation in a CO boiler.

Desorption of the $C_2$ composition (e.g., ethane and ethylene) from the sorbent is shown being carried out in sorbent unit A2 by increasing the sorbent's temperature. In this example, sweep fluid (e.g., steam) is sent to sorbent unit A2 via a line 242 and open valve V6, with the sweep fluid being at a temperature greater than the temperature at which sorption of the $C_2$ composition in the sorbent unit A2 has been carried out. The heating of the sorbent by the sweep fluid and the movement of the sweep fluid through the sorbent unit A2 causes the $C_2$ composition to desorb from the sorbent. Then the desorbed $C_2$ composition and sweep fluid are passed through open valve V8 via a line 218 and passed through sorbent unit A3 via open valve V9.

Unit A3 contains olefin-selective sorbent for sorbing ethylene from the $C_2$ composition. The sorbent is at a temperature lower than that of the hydrocarbon conversion reactor 200 and is ≥50° C. Thus, as the $C_2$ composition and sweep fluid flow through the sorbent unit A3, the ethylene is selectively sorbed and the ethane and sweep fluid exit the sorbent unit A3 via a line 222. The sweep fluid can be relatively easily condensed at non-cryogenic temperatures and separated from the ethane to recover substantially pure ethane.

In aspects shown in FIG. 2, desorption of ethylene form the sorbent is being carried out in sorbent unit A4. Desorption is facilitated by increasing the temperature of the sorbent. In this example, sweep fluid (e.g., steam) is sent to sorbent unit A4 via a line 241 and open valve V12, with the sweep fluid being at a temperature greater than the temperature at which sorption of the ethylene from the $C_2$ composition has been previously carried out. The heating of the sorbent by the sweep fluid and the movement of the sweep fluid through the sorbent unit A4 causes the ethylene to desorb from the sorbent. Then the desorbed ethylene and sweep fluid exit the sorbent unit A4 via a line 220. The sweep fluid can be relatively easily condensed at non-cryogenic temperatures and separated from the ethylene to recover substantially pure ethylene.

Figure 3A:
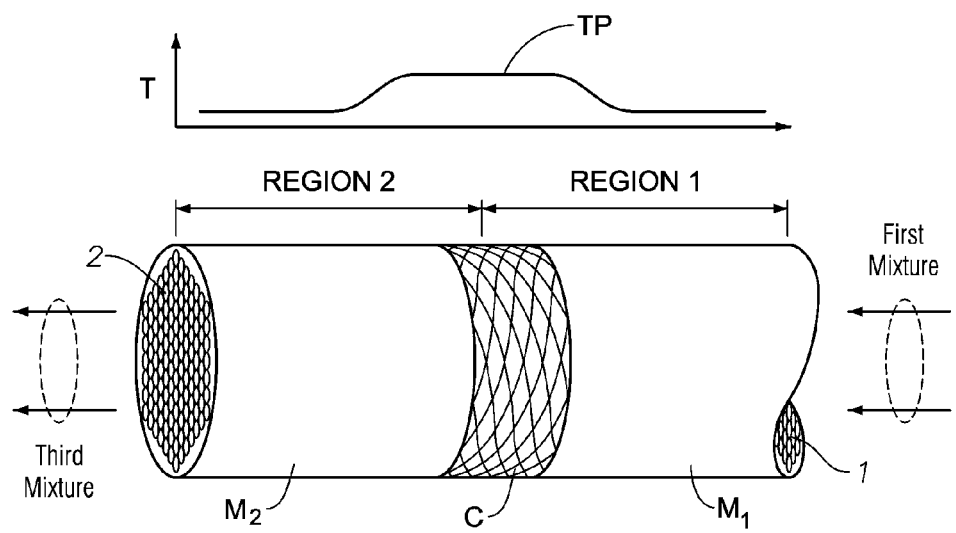
FIGS. 3A and 3B are simplified diagrammatic illustrations of a generalized reverse-flow reactor system, which can be used to carry the conversion reaction to produce $C_{2+}$ olefins and $C_2$ compositions.
Figure 3B:
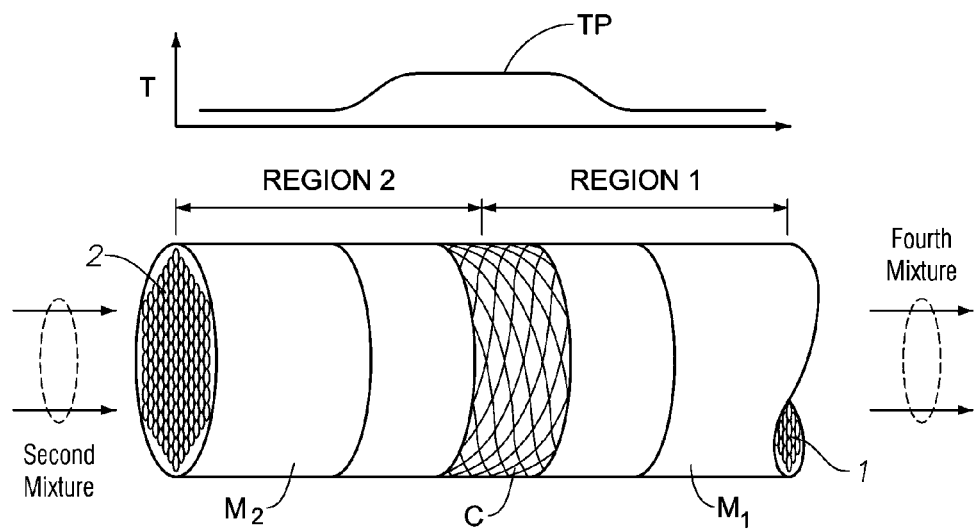

Example 3 (with Reference to FIGS. 3A and 3B)

FIGS. 3A and 3B depict aspects of a generalized reverse-flow reactor system that can be used to carry out the specified conversion reaction. Such aspects can be used as the conversion reactors 100 and 200 of FIGS. 1 and/or 2.

The reverse-flow reactor includes two regions: a first region (Region 1) and a second region (Region 2). Region 1 and Region 2 comprise a first thermal mass (M1) and a second thermal mass (M2), respectively. The thermal masses can be selected from among any of the specified thermal masses, and can be coupled together as a continuous mass or coupled in a series arrangement of mass materials. The terms first and second thermal masses are used to particularly describe the flow of heat in the reverse-flow reactor system according to regions that are heated and cooled by means of thermal mass, such that the reaction being carried out results in absorption and release of heat in a manner that is effective in continuously operating the reverse-flow reactor system.

A catalytic conversion zone (Zone C) is included in the reverse-flow reactor shown in FIGS. 3A and 3B. At least one hydrocarbon conversion catalyst is included in Zone C. At least a portion of the catalyst of the catalytic conversion Zone C can be deposited on or in the first thermal mass M1 (or a segment thereof) and/or second thermal mass M2 (or a segment thereof) of the Regions 1 and 2, e.g., in aspects where the catalytic conversion zone overlaps both Region 1 and Region 2. However, the catalyst can be completely located in either Region 1 or Region 2, and/or in a region located between Regions 1 and 2. The specified hydrocarbon conversion catalyst can be part of or attached to the thermal mass material of Region 1, Region 2, or both. Optionally, the catalyst is located in a defined sub-region of the first and/or second thermal mass, the sub-regions being proximate to the center of the reactor as shown in FIGS. 3A and 3B.

Optionally, one or more mixer means can be used between reactor regions or zones, e.g., between $M_1$ and C and/or between $M_2$ and C. Doing so is observed to improve the oxidative coupling reaction. Mixer mechanisms, distributor mechanisms, reactor system internals, flow-control mechanisms, etc., for the reactor can be substantially the same as those described in U.S. Pat. No. 7,943,808 and/or U.S. Patent Application Publication No. 2013/157205, for example.

In aspects shown in FIG. 3A, during a first time interval, a first feed mixture is passed to an inlet 1 of the reverse-flow reactor. The first feed mixture can comprise >10.0 wt. % alkane and >2.0 wt. % oxidant, the weight percents being based on total weight of the first feed mixture.

As shown in FIG. 3A, the first feed mixture passes proximate to the first thermal mass (e.g., is passed through or across the first thermal mass) M1 of Region 1, which has been previously heated to a predetermined temperature range suitable to convert components of the first feed mixture to the desired product. As the first feed mixture passes the first thermal mass M1, heat is transferred from the heated first thermal mass M1 to the first feed mixture to produce a heated first feed mixture. The heated first feed mixture passes the catalytic conversion Zone C, catalytically converting, preferably by an exothermic reaction process, at least a portion of the heated first feed mixture's alkane to produce a first reaction mixture. The first reaction mixture can comprise, e.g., $C_{2+}$ olefin produced by the alkane conversion, and any unconverted portion of the first mixture. Heat is transferred from the first reaction mixture to the second thermal mass M2, and at least a portion of the first reaction mixture is conducted away from the reverse flow-reactor by way of an exit 2 of the reverse-flow reactor, e.g., for separating olefin from the first reaction mixture. The movement of the reverse-flow reactor's temperature profile during the first time internal is represented by the arrows on curve TP. Flow of the first feed mixture to the inlet 1 is subsequently lessened or discontinued. A reverse flow can then be initiated, e.g., during a second time interval.

During a second time interval, illustrated in FIG. 3B, reverse flow is initiated by passing a second feed mixture through the exit 2 of the reverse-flow reactor, in reverse flow direction from that of the first feed mixture. The second feed mixture also comprises ≥10.0 wt. % alkane and ≥2.0 wt. % oxidant, the weight percents being based on total weight of the second mixture, and is obtained from the same source as the first feed mixture.

As shown in FIG. 3B, the second feed mixture passes proximate to the second thermal mass (e.g., is passed through or across the second thermal mass) M2 of Region 2. M2 has been previously heated as a result of the exothermic reaction previously carried out in the catalytic conversion zone C during the first time interval, e.g., by transferring heat from the first reaction mixture to M2. As the second feed mixture passes the second thermal mass M2, heat is transferred from the heated second thermal mass M2 to the second feed mixture to produce a heated second feed mixture. The heated second feed mixture passes the catalytic conversion zone C, catalytically converting, preferably by exothermic reaction, at least a portion of the heated second feed mixture's alkane to produce a second reaction mixture. The second reaction mixture comprises, e.g., $C_{2+}$ olefin produced by the specified alkane conversion, and any unconverted second feed mixture. Heat is transferred from the second reaction mixture to the first thermal mass M1, and at least a portion of the second reaction mixture is conducted away from the reverse flow-reactor by way of the inlet 1 of the reverse-flow reactor. Movement of the reverse-flow reactor's temperatures profile during the second time interval is represented by the arrows on curve TP. Flow of the second reaction mixture is subsequently lessened or discontinued. One skilled in the art will appreciate that during the second time interval (i) inlet 1 functions as an exit and (ii) exit 2 functions as an inlet.

The first and second time intervals, as generally described according to the exemplary schemes shown in FIGS. 3A and 3B, can be substantially non-overlapping intervals. Each of the first and second time intervals can be, independently, an interval having a duration in the range of from about 0.5 seconds to about 15 seconds. The interval between the first and second time intervals (the "dead-time", which represents the interval of time it takes to reverse flow of the feed mixtures) is preferably as short as possible so that the reverse flow cycle can be as rapid as possible. From a practical standpoint, the dead-time should be, e.g., ≤than 0.5 seconds, such as in a range of from about 0.01 seconds to about 0.5 seconds. Upon completion of the second time interval, the intervals can be repeated. That is, the flow shown in FIG. 3A can be reinitiated and followed by subsequent reinitiation of the flow shown in FIG. 3B.

In aspects shown in FIGS. 3A and 3B, the oxidant can comprise ≥10.0% (molar basis) of $O_2$ in air and/or of $O_2$ obtained from air. The alkane can comprise ≥10.0% (molar basis) of one or more of $C_1$ to $C_5$ linear, iso, and cyclo alkane.

Aspects shown in FIGS. 3A and 3B can be used as the hydrocarbon conversion reactors 100 and 200 in FIGS. 1 and 2 respectively. In such an instance, the first and second reaction mixtures shown in FIGS. 3A and 3B can be sent via the respective lines 106 and 206 in FIGS. 1 and 6 for further processing by the various selective removal of $CO_2$ and water, and particularly for selective $C_2$ separation by a selective $C_2$ sorption system.

In other aspects (not shown), at least a portion of the separated olefin can be polymerized. For example, in certain aspects in which the separated olefin comprises ethylene, the ethylene is polymerized, e.g., to produce a polyethylene composition.

Referring to FIGS. 3A and 3B for further examples of the mixtures that can be used, the first feed mixture's oxidant stream can comprise ≥99.0 wt. % of $O_2$, e.g., $O_2$ obtained from air, based on total weight of the first feed mixture's oxidant. The first feed mixture's alkane stream can comprise ≥99.0 wt. % methane based on total weight of the first feed mixture's alkane. Additionally, the first feed mixture can have a methane:molecular oxygen molar ratio in the range of 10.0 to 20.0. When the oxidant of the first feed mixture comprises $O_2$ in air, the $N_2$ and other gases in the air are considered to be diluent components of the total feed, not oxidant components.

The second feed mixture's oxidant stream, with further reference to FIGS. 3A and 3B, can also comprise ≥99.0 wt. % of $O_2$, e.g., $O_2$ obtained from air, based on total weight of the second mixture's oxidant. The second feed mixture's alkane stream can comprise ≥99.0 wt. % methane based on the weight of the second feed mixture's alkane. Additionally, the second feed mixture can have a methane:molecular oxygen molar ratio in the range of 10.0 to 20.0. When the second feed mixture comprises $O_2$ in air, the $N_2$ and other gases in the air are considered to be diluent components of the total feed, not oxidant components.

The invention is not limited to aspects shown only in the Figures. For example, in other aspects, hydrocarbon conversion reactor can comprise a honeycomb monolith in the form of an elongated polygonal body. The honeycomb can comprise two or more portions, the portions being in side-to-side contact, with each section having one or more flow passages feeding into a flow passage in the adjacent portion. That is, the portions can be adjacent to each other, with each upstream of the mixing means or each downstream of the mixing means.

In other aspects, the hydrocarbon conversion reactor can include three, four, five, six or more thermal masses, each thermal mass having one or more than one reaction zone. The reactor zones in the hydrocarbon conversion reactor can be adjacent to each other or may optionally have a mixing means (e.g., mixing components or a gap) disposed between the portions.

While the present invention has been described and illustrated with respect to certain aspects, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A process for producing and isolating a $C_2$ composition comprising:
    (a) providing first and second hydrocarbon reactants and first and second oxidants, wherein the first and second hydrocarbon reactants each comprise $\geq 10\%$ methane (molar basis, per mole of hydrocarbon reactant) and the first and second oxidants each comprise $O_2$;
    (b) catalytically converting at least a portion of the first hydrocarbon reactant in the presence of the first oxidant and an oxidative methane coupling catalyst to produce a first reaction mixture comprised of (A) a $C_2$ composition produced by the catalytic conversion, (B) water and/or $CO_2$ produced during the catalytic conversion, and (C) unconverted methane, wherein
        i) the catalytic conversion includes catalytic oxidative methane coupling carried out in a reverse-flow reactor, the reverse-flow reactor comprising a heated first thermal mass comprising $\geq 50.0$ wt. % of a first sorbent, based on total weight of the first thermal mass, a second thermal mass comprising $\geq 50.0$ wt. % of a second sorbent, based on total weight of the second thermal mass, and the oxidative methane coupling catalyst;
        ii) the first reaction mixture is produced by combining the first hydrocarbon reactant and the first oxidant at a methane:$O_2$ molar ratio of $>2:1$, and
        iii) the catalytic conversion is carried out in a first time interval, and the first interval includes the steps of:
    I passing the first hydrocarbon reactant and the first oxidant to the reverse-flow reactor;
    II transferring heat from the heated first thermal mass to at least one of the first hydrocarbon reactant and the first oxidant and combining the hydrocarbon reactant and the first oxidant to produce a first heated feedstock mixture;
    III producing the first reaction mixture by carrying out step (b) using the first hydrocarbon reactant and the first oxidant of the first heated feedstock mixture;
    IV transferring heat from the first reaction mixture to the second thermal mass to produce a heated second thermal mass;
    (c) exposing the first reaction mixture to the second sorbent under kinetic sorption conditions to selectively remove from the first reaction mixture at least a portion of the first reaction mixture's $C_2$ composition to produce a first $C_2$ lean mixture comprised of at least a portion of the unconverted methane, wherein
        (i) the first $C_2$ lean mixture has a $C_2$ content less than that of the first reaction mixture, and
        (ii) the sorbent comprises $C_2$ selective sorbent having a selectivity for [ethane+ethylene] over that of methane $>1.0$; and
    (d) lessening or discontinuing the passing of the first hydrocarbon reactant and the first oxidant to the reverse-flow reactor.

2. The process of claim 1, wherein $\geq 50.0$ wt. % of the first thermal mass, based on total weight of the first thermal mass, is located in a first region of the reverse-flow reactor, $\geq 50.0$ wt. % of the second thermal mass, based on total weight of the second thermal mass, is located in a second region of the reverse-flow reactor, and $\geq 50$ wt. % of the oxidative methane coupling catalyst, based on total of the oxidative methane coupling catalyst, is located in a third region of the reverse-flow reactor, the third region being located between the first and second regions.

3. The process of claim 2, wherein the catalytic conversion is further carried out in a second time interval following the first time interval and the second time interval includes the steps of:
    i. passing the second hydrocarbon reactant and the second oxidant to the reverse-flow reactor;
    ii. transferring heat from the heated second thermal mass to at least one of the second hydrocarbon reactant and the second oxidant and combining the second hydrocarbon reactant and the second oxidant to produce a second heated feedstock mixture;
    iii. producing a second reaction mixture by catalytically converting at least a portion of the second hydrocarbon reactant in the presence of the second oxidant and the oxidative methane coupling catalyst, the second reaction mixture comprising (A) a $C_2$ composition produced by the catalytic conversion, (B) water and/or CO2 produced during the catalytic conversion, and (C) unconverted methane;
    iv. transferring heat from the second reaction mixture to the first thermal mass to produce a re-heated first thermal mass; and
    v. exposing the second reaction mixture to the first sorbent under kinetic sorption conditions to selectively remove from the second reaction mixture at least a portion of the second reaction mixture's $C_2$ composition to produce a second $C_2$ lean mixture, wherein
        (A) the second $C_2$ lean mixture comprises at least a portion of the second reaction mixture's unconverted methane,
        (B) the second $C_2$ lean mixture has a $C_2$ content less than that of the second reaction mixture; and
        (C) the sorbent comprises $C_2$ selective sorbent having a selectivity for [ethane+ethylene] over that of methane $>1.0$; and
    vi. lessening or discontinuing the passing of the second reactant and the second oxidant to the reverse-flow reactor.

4. The process of claim 3 wherein the same $C_2$ selective sorbent is utilized in both of (A) step v of the first time interval and (B) step v of the second time interval.

5. The process of claim 3 wherein a first $C_2$ selective sorbent is utilized in step v of the first time interval, a second $C_2$ selective sorbent is utilized in step v of the second time interval, and the first and second $C_2$ selective sorbents have substantially the same composition.

6. The process of claim 3, further comprising desorbing ethylene from the $C_2$ selective sorbent of step v of the first time interval and/or desorbing ethylene from the $C_2$ selective sorbent of step v of the second time interval.

7. A hydrocarbon conversion process, comprising:
    a. providing a first reactant and a first oxidant, wherein the first reactant comprises $\geq 10.0\%$ $C_{5-}$ alkane (molar basis, per mole of first reactant) and the first oxidant comprises $O_2$;
    b. providing a second reactant and a second oxidant, wherein the second reactant comprises $\geq 10.0\%$ $C_{5-}$ alkane (molar basis, per mole of second reactant) and the second oxidant comprises $O_2$;

c. providing a reverse-flow reactor comprising a heated first thermal mass comprising ≥50.0 wt. % of a first sorbent, based on total weight of the first thermal mass, a second thermal mass comprising ≥50.0 wt. % of a second sorbent, based on total weight of the second thermal mass, and at least one oxidative methane coupling catalyst;
d. during a first time interval,
i. passing the first reactant and the first oxidant to the reverse-flow reactor;
ii. transferring heat from the heated first thermal mass to at least one of the first reactant or first oxidant and combining the first reactant and first oxidant to produce a first feedstock mixture, the first feedstock mixture having a methane:$O_2$ molar ratio ≥2.0;
iii. catalytically converting at least a portion of the first feedstock's mixture's $C_{5-}$ alkane in the presence of the oxidative methane coupling catalyst to produce a first reaction mixture, the first reaction mixture comprising (A) ethylene produced by the alkane conversion and (B) unconverted $C_{5-}$ alkane, wherein the catalytic conversion includes catalytic oxidative methane coupling;
iv. transferring heat from the first reaction mixture to the second thermal mass;
v. exposing the first reaction mixture to the second sorbent to selectively sorb ethylene from the first reaction mixture to produce a first ethylene-lean mixture, wherein
(A) the first ethylene-lean mixture comprises at least a portion of the first reaction mixture's unconverted $C_{5-}$ alkane,
(B) the first ethylene-lean mixture has an ethylene content less than that of the first reaction mixture; and
(C) the second sorbent comprises olefin-selective sorbent; and
vi. lessening or discontinuing the passing of the first mixture to the reverse-flow reactor; and
e. during a second time interval,
i. passing the second reactant and second oxidant to the reverse-flow reactor;
ii. transferring heat from the heated second thermal mass to at least one of the second reactant or second oxidant and combining the second reactant and second oxidant to produce a second feedstock mixture, the second feedstock mixture having a methane:$O_2$ molar ratio ≥2.0;
iii. catalytically converting at least a portion of the second feedstock mixture's methane in the presence of the oxidative methane coupling catalyst to produce a second reaction mixture, the second reaction mixture comprising (A) ethylene produced by the catalytic conversion and (B) unconverted C2 composition, wherein the catalytic conversion includes catalytic oxidative methane coupling;
iv. transferring heat from the second reaction mixture to the first thermal mass to re-heat the first thermal mass;
v. exposing the second reaction mixture under kinetic sorption conditions to the first sorbent to selectively sorb ethylene from the second reaction mixture to produce an ethylene-lean mixture, wherein
(A) the second ethylene-lean mixture comprises at least a portion of the second reaction mixture's unconverted $C_{5-}$ alkane,
(B) the second ethylene-lean mixture has an ethylene content less than that of the second reaction mixture; and
(C) the first sorbent comprises olefin-selective sorbent; and
vi. lessening or discontinuing the passing of the second mixture to the reverse-flow reactor.

8. The process of claim 7, further comprising desorbing at least a portion of the sorbed ethylene from the first sorbent after step (e) vi and/or desorbing at least a portion of the sorbed ethylene from the second C2 selective sorbent after step (d) vi.

* * * * *